United States Patent
Fan et al.

(10) Patent No.: US 12,421,547 B2
(45) Date of Patent: Sep. 23, 2025

(54) HIGH THROUGHPUT MULTIOMICS SAMPLE ANALYSIS

(71) Applicant: Becton, Dickinson and Company, Franklin Lakes, NJ (US)

(72) Inventors: Christina Fan, Franklin Lakes, NJ (US); Elisabeth Marie Walczak, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

(21) Appl. No.: 18/324,880

(22) Filed: May 26, 2023

(65) Prior Publication Data

US 2023/0295723 A1    Sep. 21, 2023

Related U.S. Application Data

(63) Continuation of application No. 16/400,885, filed on May 1, 2019, now Pat. No. 11,773,441.

(60) Provisional application No. 62/666,483, filed on May 3, 2018.

(51) Int. Cl.
    *C12Q 1/6876* (2018.01)

(52) U.S. Cl.
    CPC .................................. *C12Q 1/6876* (2013.01)

(58) Field of Classification Search
    CPC ...... C12Q 1/68; C12Q 1/6876; C12Q 1/6806; C12Q 1/6869
    See application file for complete search history.

(56) References Cited

U.S. PATENT DOCUMENTS

| | | | |
|---|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |

(Continued)

FOREIGN PATENT DOCUMENTS

| CA | 2474509 A1 | 2/2003 |
|---|---|---|
| CN | 103443338 A | 12/2013 |

(Continued)

OTHER PUBLICATIONS

Dey et al., Integrated genome and transcriptome sequencing of the same cell. Nature Biotechnology 33(3) : 285 (Year: 2015).*
Sos et al. Characterization of chromatin accessibility with a transposome hypersensitive sites sequencing (THS-seq) assay Genome Biology 17 :20 (15 pgs) (Year: 2016).*
Tsompana et al., Chromatin Accessibility : a window into the genome. Epigenetics & Chromatin 7:33 (Year: 2014).*
10X Genomics, Inc., 2019, User Guide: Visium Spatial Gene Expression Reagent Kits, 10xGenomics.com, 76 pp.

(Continued)

*Primary Examiner* — Ethan C Whisenant

(74) *Attorney, Agent, or Firm* — Dickinson Wright PLLC

(57) ABSTRACT

Disclosed herein include systems, methods, compositions, and kits for sample analysis. Nucleic acid fragments comprising a capture sequence (or a complement thereof) can be generated from double-stranded genomic deoxyribonucleic acid (gDNA), barcoded to generate single-stranded DNA (ssDNA) fragments, and sequenced. Information relating to the gDNA (e.g., genome, chromatin accessibility, methylome) can be determined based on the sequences of the ssDNA fragments in the sequencing data obtained.

30 Claims, 7 Drawing Sheets

(56) References Cited

U.S. PATENT DOCUMENTS

| | | |
|---|---|---|
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,567,646 B2 | 2/2017 | Fan et al. |
| 9,582,877 B2 | 2/2017 | Fu et al. |
| 9,593,365 B2 | 3/2017 | Frisen et al. |
| 9,644,204 B2 | 5/2017 | Hindson et al. |
| 9,677,131 B2 | 6/2017 | Fredriksson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 11,092,607 B2 | 8/2021 | Gaublomme et al. |
| 11,460,468 B2 | 10/2022 | Fan et al. |
| 11,467,157 B2 | 10/2022 | Fan et al. |
| 11,535,882 B2 | 12/2022 | Fu et al. |
| 11,773,441 B2 * | 10/2023 | Fan .................. C12Q 1/6876 435/6.11 |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |

(56) References Cited

U.S. PATENT DOCUMENTS

| | | |
|---|---|---|
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |

(56) References Cited

U.S. PATENT DOCUMENTS

| | | |
|---|---|---|
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1* | 10/2015 | Fan .................. C12N 15/1075 506/4 |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2016/0362730 A1 | 12/2016 | Alexander et al. |
| 2017/0044525 A1 | 2/2017 | Kaper et al. |
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0002738 A1 | 1/2018 | Wang et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0245069 A1* | 8/2018 | DeSantis ............... C12N 11/06 |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0320241 A1 | 11/2018 | Nolan et al. |
| 2018/0340169 A1 | 11/2018 | Belhocine et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |

(56) References Cited

U.S. PATENT DOCUMENTS

| | | |
|---|---|---|
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |
| 2023/0083422 A1 | 3/2023 | Fu et al. |
| 2023/0109336 A1 | 4/2023 | Shum et al. |
| 2023/0125113 A1 | 4/2023 | Fan et al. |

FOREIGN PATENT DOCUMENTS

| | | |
|---|---|---|
| CN | 105705659 A | 6/2016 |
| DE | 102008025656 | 12/2009 |
| EP | 1473080 A2 | 11/2004 |
| EP | 1647600 A2 | 4/2006 |
| EP | 1845160 A1 | 10/2007 |
| EP | 2036989 A1 | 3/2009 |
| EP | 1379693 B1 | 5/2009 |
| EP | 2204456 A1 | 7/2010 |
| EP | 2431465 A1 | 3/2012 |
| EP | 2203749 B1 | 8/2012 |
| EP | 2511708 A1 | 10/2012 |
| EP | 2538220 A1 | 12/2012 |
| EP | 2623613 A1 | 8/2013 |
| EP | 1745155 B1 | 10/2014 |
| EP | 2805769 A1 | 11/2014 |
| EP | 2556171 B1 | 9/2015 |
| EP | 2970958 B1 | 12/2017 |
| EP | 3263715 A1 | 1/2018 |
| EP | 2670863 B1 | 6/2018 |
| EP | 3136103 B1 | 8/2018 |
| EP | 2954102 B1 | 12/2018 |
| EP | 3428290 A1 | 1/2019 |
| EP | 2970957 B1 | 4/2019 |
| EP | 3058092 B1 | 5/2019 |
| EP | 3256606 B1 | 5/2019 |
| EP | 3327123 B1 | 8/2019 |
| GB | 2293238 A | 3/1996 |
| JP | H04108385 | 4/1992 |
| JP | 2001078768 A | 3/2001 |
| JP | 2005233974 A | 9/2005 |
| JP | 2007504831 A | 3/2007 |
| JP | 2008256428 A | 10/2008 |
| JP | 2012-506704 | 3/2012 |
| JP | 2013039275 A | 2/2013 |
| JP | 2016-533187 | 10/2016 |
| JP | 2018-501776 | 1/2018 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001020035 | 3/2001 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |

(56) References Cited

FOREIGN PATENT DOCUMENTS

| | | |
|---|---|---|
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013137737 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 12/2015 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018/018008 | 1/2018 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020219721 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO20210178199 | 9/2021 |
| WO | WO2021247593 | 12/2021 |
| WO | WO2022015667 | 1/2022 |
| WO | WO2022026909 | 2/2022 |

(56) References Cited

FOREIGN PATENT DOCUMENTS

| WO | WO2022040453 | 2/2022 |
|---|---|---|
| WO | WO2022143221 | 7/2022 |
| WO | WO2022256324 | 12/2022 |
| WO | WO2023/034739 | 3/2023 |
| WO | WO2023/034789 | 3/2023 |
| WO | WO2023/034790 | 3/2023 |
| WO | WO2023/034794 | 3/2023 |
| WO | WO2023/034872 | 3/2023 |
| WO | WO2023/039433 | 3/2023 |

OTHER PUBLICATIONS

10X Genomics, Inc., 2022, "Chromium Fixed RNA Profiling Reagent Kits," 10xGenomics.com, User Guide, in 95 pages.
2018 Top 10 Innovations, The Scientist Magazine® (2018). Available at: https://thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Adey et al., "Rapid, low-input, low-bias construction of shotgun fragment libraries by high-density in vitro transposition," Genome Biology 2010, 11(R19), in 17 pages.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Advisory Action dated May 31, 2023 in U.S. Appl. No. 16/789,311.
Agasti et al., "Photocleavable DNA barcode-antibody conjugates allow sensitive and multiplexed protein analysis in single cell," J Am Chem Soc. 2012, 134(45), 18499-18502.
Ahern, "Biochemical, Reagent Kits Offer Scientists Good Return on Investment," The Scientist 1995, 9(15), in 5 pages.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Arguel et al., "A cost effective 5' selective single cell transcriptome profiling approach with improved UMI design," Nucleic Acids Research 2017, 45(7), e48, in 11 pages.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, Aug. 21, 2010, "Useful fundamental numbers in molecular biology," 2001-2004. http://bionumbers.hms.harvard.edu/KeyNumbers/aspx, 1-4.
Biosciences Product Catalogue, Dynal® Catalog 1999, Oslo, Norway, 49-51.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.

(56) References Cited

OTHER PUBLICATIONS

Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research 2002, 8, 2580-2585.
Chang et al., "Single-cell protein and gene expression profiling of stem memory T cells by BD Ab-seq," Annual Joint Meeting of the American Society for Cell Biology and the European Molecular Biology Organization 2017, 28(26), P1896.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Chen et al., "High-throughput sequencing of the transcriptome and chromatin accessibility in the same cell," Nature Biotechnology 2019, 37, 1452-1457.
Church et al., "Multiplex DNA sequencing," Science 1988, 240(4849), 185-188.
Clontech Laboratories, Inc., "Smart™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
De Simone et al., "Single Cell T Cell Receptor Sequencing: Techniques and Future Challenges," Frontiers in Immunology 2018, 9(1638), 1-7.
Decision of Refusal dated Aug. 21, 2017 in Japanese Patent Application No. 2014-558975.
Delley et al., "Combined aptamer and transcriptome sequencing of single cells," bioRxiv 2017, 1-10.
Dengl et al., "Engineered hapten-binding antibody derivatives for modulation of pharmacokinetic properties of small molecules and targeted payload delivery," Immunol Rev. 2016, 270, 165-177.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dovgan et al., "Antibody-Oligonucleotide Conjugates as Therapeutic, Imaging, and Detection Agents," Bioconjugate Chem. 2019, 30, 2483-2501.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.

(56) References Cited

OTHER PUBLICATIONS

Examination Report dated Jul. 6, 2020 in European Patent Application No. 17781265.8.
Examination Report dated Sep. 21, 2020 in European Patent Application No. 18703156.2.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Extended European Search Report dated May 6, 2021 in European Patent Application No. 20207621.2.
Extended European Search Report dated May 28, 2021 in European Patent Application No. 20209777.0.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
Final Office Action dated Apr. 25, 2023 in U.S. Appl. No. 16/525,054.
Final Office Action dated May 15, 2023 in U.S. Appl. No. 16/551,638.
Final Office Action dated May 19, 2023 in U.S. Appl. No. 17/163,177.
Final Office Action dated May 31, 2023 in U.S. Appl. No. 16/934,530.
Final Office Action dated Jun. 8, 2023 in U.S. Appl. No. 17/147,283.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Fitzgerald and Grivel, "A Universal Nanoparticle Cell Secretion Capture Assay," Cytometry Part A 2012, 83A(2), 205-211.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.

(56) References Cited

OTHER PUBLICATIONS

Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gertz et al., "Transposase mediated construction of RNA-seq libraries," Genome Research 2012, 22, 134-141.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Grant et al., "SNP genotyping on a genome-wide amplified DOP-PCR template," Nucleic Acids Res 2002, 30(22), e25, 1-6.
Gratton et al., "Cell-permeable peptides improve cellular uptake and therapeutic gene delivery of replication-deficient viruses in cells and in vivo," Nature Medicine 2003, 9(3), 357-362.
Grounds for Opposition dated Jul. 21, 2016 and filed in European Patent 2414548B1.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwantedhigh-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State inMammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.

(56) References Cited

OTHER PUBLICATIONS

International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Fees dated May 25, 2021 in PCT Application No. PCT/US2021/01598.
Invitation to Pay Additional Search Fees dated May 7, 2020 in PCT Application No. PCT/US2020/017890.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from aretroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Jiang et al., "Synthetic spike-in standards for RNA-seq experiments," Genome Res. 2011, 21, 1543-1551.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting DrugResistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.

(56) References Cited

OTHER PUBLICATIONS

Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., VarScan: variant detection in massively parallel sequencing of individual and pooled samples, Bioinformatics 2009, 25(17), 2283-2285.
Kolodziejczyk et al., The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.
Kotake et al., "A simple nested RT-PCR method for quantitation of the relative amounts of multiple cytokine mRNAs in small tissue samples," Journal of Immunological Methods 1996, 199, 193-203.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lake et al., "Integrative single-cell analysis of transcriptional and epigenetic states in the human adult brain," Nature Biotechnology 2018, 36(1), 70-80.
Lamble et al., "Improved workflows for high throughput library preparation using the transposome-based nextera system," BMC Biotechnology 2013, 13, 104, 1-10.
Lan et al., "Droplet barcoding for massively parallel single-molecule deep sequencing," Nature Communications 2016, 7(11784), in 10 pages.
Larson et al., "A single molecule view of gene expression," Trends Cell Biol. 2009, 19(11), 630-637.
Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343, 1360-1363.
Lee et al., "Universal process-inert encoding architecture for polymer microparticles," Nature Materials 2014, 13(5), 524-529.
Lee et al., "Comparison of Surface Markers between Human and Rabbit Mesenchymal Stem Cells," PLoS One 2014, 9(11), in 10 pages.
Lin et al., "Self-Assembled Combinatorial Encoding Nanoarrays for Multiplexed Biosensin," Nano Lett. 2007, 7 (2), 507-512.

Liu et al., "Single-cell transcriptome sequencing: recent advances and remaining challenges," F1000Research 2016, 5(F1000 Faculty Rev)(182), 1-9.
Livingstone, "rRNA depletion, poly(A) enrichment, or exonuclease treatment?" Tebu-Bio Blog 2015, in 1 page.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," ThermoFisher Scientific, Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Lutz et al., "Isolation and analysis of high quality nuclear DNA with reduced organellar DNA for plant genome sequencing and resequencing," BMC Biotechnology 2011, 11(54), in 9 pages.
Maamar et al., "Noise in Gene Expression Determines Cell Fate in Bacillus subtilis," Science 2007, 317, 526-529.
MacAulay et al., "Single Cell Genomics: Advances and Future Perspectives," PLoS Genetics 2014, 10(1), 1-9.
MacAulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Mair et al., "A Targeted Multi-omic Analysis Approach Measures Protein Expression and Low-Abundance Transcripts on the Single-Cell Level", Cell Reports 2020, 31(1), 107499, in 20 pages.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
Mayer et al., "Obtaining deeper insights into microbiome diversity using a simple method to block host and nontargets in amplicon sequencing," Molecular Ecology Resources 2021, 21(6), 1952-1965.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Meyer et al., "Parallel tagged sequencing on the 454 platform," Nature Protocols 2008, 3(2), 267-278.

(56) References Cited

OTHER PUBLICATIONS

Miller et al., Directed evolution by in vitro compartmentalization, Nature Methods 2006, 3(7), 561-570.

Miner et al., "Molecular barcodes detect redundancy and contamination in hairpin-bisulfite PCR," Nucleic Acids Research 2004, 32(17), e135, 1-4.

Minnoye et al., "Chromatin accessibility profiling methods," Nature Reviews Method Primers 2021, 1-24.

Monneron, "One-step Isolation and Characterization of Nuclear Membranes, 1974 Electron Microscopy and Composition of Biological Membranes and Envelops," The Royal Publishing Society 1974, 268, 101-108.

Mortazavi et al., "Mapping and quantifying mammalian transcriptomes by RNA-Seq," Nat. Methods 2008, 5(7), 621-628.

Nadai et al., Protocol for nearly full-length sequencing of HIV-1 RNA from plasma, PLoS One 2008, 3(1), e1420, 1-6.

Nagai et al., "Development of a microchamber array for picoleter PCR," Anal. Chem. 2001, 73, 1043-1047.

Navin et al., "The first five years of single-cell cancer genomics and beyond," Genome Research 2015, 25, 1499-1507.

Newell et al., Cytometry by time-of-flight shows combinatorial cytokine expression and virus-specific cell niches within a continuum of CD8+ T cell phenotypes. Immunity 2012, 36(1), 142-152.

Non-Final Office Action dated Oct. 3, 2013 in U.S. Appl. No. 12/969,581.

Non-Final Office Action dated Feb. 18, 2015 for U.S. Appl. No. 14/540,007.

Non-Final Office Action dated Feb. 26, 2015 for U.S. Appl. No. 14/540,029.

Non-Final Office Action dated Mar. 19, 2015 in U.S. Appl. No. 14/540,018.

Non-Final Office Action dated May 7, 2015 for U.S. Appl. No. 13/327,526.

Non-Final Office Action dated Dec. 3, 2015 for U.S. Appl. No. 14/281,706.

Non-Final Office Action dated Dec. 31, 2015 for U.S. Appl. No. 14/800,526.

Non-Final Office Action dated Apr. 11, 2016 in U.S. Appl. No. 14/472,363.

Non-Final Office Action dated May 10, 2016 in U.S. Appl. No. 14/381,488.

Non-Final Office Action dated May 13, 2016 in U.S. Appl. No. 14/508,911.

Non-Final Office Action dated Aug. 17, 2016 for U.S. Appl. No. 14/800,526.

Non-Final Office Action dated Sep. 26, 2016 in U.S. Appl. No. 15/167,807.

Non-Final Office Action dated Oct. 11, 2016 in U.S. Appl. No. 15/224,460.

Non-Final Office Action dated Jan. 19, 2017 in U.S. Appl. No. 15/055,445.

Non-Final Office Action dated Mar. 24, 2017 in U.S. Appl. No. 15/409,355.

Non-Final Office Action dated Jun. 2, 2017 in U.S. Appl. No. 14/381,526.

Non-Final Office Action dated Jun. 7, 2017 in U.S. Appl. No. 14/381,488.

Non-Final Office Action dated Jul. 28, 2017 in U.S. Appl. No. 14/975,441.

Non-Final Office Action dated Sep. 8, 2017 in U.S. Appl. No. 15/046,225.

Non-Final Office Action dated Sep. 8, 2017 in U.S. Appl. No. 15/134,967.

Non-Final Office Action dated Nov. 1, 2017 in U.S. Appl. No. 15/667,125.

Non-Final Office Action dated Nov. 9, 2017 in U.S. Appl. No. 15/004,618.

Non-Final Office Action dated Jan. 9, 2018 in U.S. Appl. No. 15/217,896.

Non-Final Office Action dated Jan. 12, 2018 in U.S. Appl. No. 15/217,886.

Non-Final Office Action dated Mar. 8, 2018 in U.S. Appl. No. 15/608,780.

Non-Final Office Action dated Apr. 6, 2018 in U.S. Appl. No. 15/603,239.

Non-Final Office Action dated Jul. 25, 2018 in U.S. Appl. No. 15/108,268.

Non-Final Office Action dated Oct. 4, 2018 in U.S. Appl. No. 15/260,106.

Non-Final Office Action dated Oct. 25, 2018 in U.S. Appl. No. 16/012,584.

Non-Final Office Action dated Nov. 5, 2018 in U.S. Appl. No. 16/038,790.

Non-Final Office Action dated Nov. 26, 2018 in U.S. Appl. No. 15/937,713.

Non-Final Office Action dated Jan. 7, 2019 in U.S. Appl. No. 15/055,407.

Non-Final Office Action dated Jan. 14, 2019 in U.S. Appl. No. 16/219,553.

Non-Final Office Action dated Mar. 19, 2019 in U.S. Appl. No. 15/046,225.

Non-Final Office Action dated May 15, 2019 in U.S. Appl. No. 15/084,307.

Non-Final Office Action dated May 23, 2019 in U.S. Appl. No. 15/459,977.

Non-Final Office Action dated Jun. 17, 2019 in U.S. Appl. No. 14/381,488.

Non-Final Office Action dated Jul. 9, 2019 in U.S. Appl. No. 15/596,364.

Non-Final Office Action dated Aug. 20, 2019 for U.S. Appl. No. 15/715,028.

Non-Final Office Action dated Sep. 18, 2019 in U.S. Appl. No. 16/194,819.

Non-Final Office Action dated Nov. 29, 2019 in U.S. Appl. No. 15/937,713.

Non-Final Office Action dated Jan. 17, 2020 in U.S. Appl. No. 15/084,307.

Non-Final Office Action dated Feb. 5, 2020 in U.S. Appl. No. 15/875,816.

Non-Final Office Action dated Mar. 12, 2020 in U.S. Appl. No. 16/789,358.

Non-Final Office Action dated Mar. 17, 2020 in U.S. Appl. No. 15/055,407.

Non-Final Office Action dated Mar. 26, 2020 in U.S. Appl. No. 16/012,635.

Non-Final Office Action dated Mar. 26, 2020 in U.S. Appl. No. 16/789,311.

Non-Final Office Action dated Jun. 8, 2020 in U.S. Appl. No. 15/715,028.

Non-Final Office Action dated Aug. 4, 2020 in U.S. Appl. No. 15/459,977.

Non-Final Office Action dated Aug. 19, 2020 in U.S. Appl. No. 16/374,626.

Non-Final Office Action dated Aug. 25, 2020 in U.S. Appl. No. 14/381,488.

Non-Final Office Action dated Dec. 4, 2020 in U.S. Appl. No. 16/677,012.

Non-Final Office Action dated Dec. 9, 2020 in U.S. Appl. No. 16/788,743.

Non-Final Office Action dated Jan. 19, 2021 in U.S. Appl. No. 16/836,750.

Non-Final Office Action dated Feb. 2, 2021 in U.S. Appl. No. 16/535,080.

Non-Final Office Action dated Feb. 25, 2021 in U.S. Appl. No. 15/055,407.

Non-Final Office Action dated Feb. 25, 2021 in U.S. Appl. No. 15/084,307.

Non-Final Office Action dated Mar. 29, 2021 in U.S. Appl. No. 16/789,358.

Non-Final Office Action dated Apr. 14, 2021 in U.S. Appl. No. 16/789,311.

(56) References Cited

OTHER PUBLICATIONS

Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Non-Final Office Action dated Apr. 26, 2023 in U.S. Appl. No. 16/540,971.
Non-Final Office Action dated Apr. 26, 2023 in U.S. Appl. No. 16/374,626.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Mar. 20, 2019 in U.S. Appl. No. 16/219,553.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Sep. 23, 2020 in Korean Patent Application No. 10-2016-7008144.
Notice of Allowance dated Oct. 29, 2020 in U.S. Appl. No. 15/987,851.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean Patent Application No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 26, 2022 in Chinese Patent Application No. 201780058799.1.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.

(56) References Cited

OTHER PUBLICATIONS

Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Notice of Allowance dated Jun. 8, 2023 in U.S. Appl. No. 16/459,444.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application No. 2017800587991.

(56) References Cited

OTHER PUBLICATIONS

Office Action dated Feb. 9, 2022 in Japanese Patent Application No. 2019-540515.
Office Action dated Mar. 7, 2022 in Korean Patent Application No. 10-2022-7004715.
Office Action dated May 5, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.
Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Nov. 24, 2022 in Chinese Patent Application No. 2018800147939.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Office Action dated Apr. 24, 2023 in European Patent Application No. 21714995.4.
Office Action dated Apr. 26, 2023 in European Patent Application No. 18703156.2.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated Jun. 1, 2023 in Japanese Patent Application No. 2020-561807.
Ogino et al., "Quantification of PCR bias caused by a single nucleotide polymorphism in SMN gene dosage analysis," J Mol Diagn. 2002, 4(4), 185-190.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Ozkumur et al., "Inertial Focusing for Tumor Antigen-Dependent and -Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) cDNA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes andsample integrity: BestKeeper—Excel-based tool using pair-wise correlations," Biotechnology Letters 2004, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Qiu et al., "DNA Sequence-Based "Bar Codes" for Tracking the Origins of Expressed Sequence Tagsfrom a Maize cDNA Library Constructed Using Multiple mRNA Sources," Plant Physiol. 2003, 133, 475-481.
Quail et al., "SASI-Seq: sample assurance Spike-Ins, and highly differentiating 384 barcoding for Illumina sequencing," BMC Genomics 2014, 15(110), in 13 pages.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Restriction Requirement dated Mar. 15, 2016 in U.S. Appl. No. 14/381,488.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.

(56) References Cited

OTHER PUBLICATIONS

Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 4, 2023 in U.S. Appl. No. 17/161,558.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Schmitt et al., "Detection of ultra-rare mutations by next-generation sequencing," Proc Natl Acad Sci 2012, 109(36), 1-6.
Schouten et al., "Relative quantification of 40 nucleic acid sequences by multiplex ligation-dependent probe amplification," Nucleic Acids Research 2002, 30(12), e57.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shapiro et al., "Single-cell sequencing-based technologies will revolutionize whole-organism science," Nature Reviews Genetics 2013, 14, 618-629.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.Ko, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy Number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stoeckius et al., "Large-scale simultaneous measurement of epitopes and transcriptomes in single cells," Nature Methods 2017, 14(9), 865-868.
Stoeckius et al., "Cell Hashing with barcoded antibodies enables multiplexing and doublet detection for single cell genomics," Genome Biology 2018, 19(224), 1-12.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons to Attend Oral Proceedings dated Nov. 16, 2020 in European Patent Application No. 17202409.3.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for mycobacterium tuberculosis DNA," Journal of Clinical Microbiology 2006, 44, 1029-1039.
Takara Bio, "SMARTer Human BCR IgG IgM H/K/L Profiling Kit User Manual," Takara Bio USA Inc. 2019, 1-22.
Tan et al., "Genome-wide comparison of DNA hydroxymethylation in mouse embryonic stem cells andneural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
TotalSeq™-A0251 anti-human Hashtag 1 Antibody, BioLegend®, Jul. 2018, 1-10.

(56) References Cited

OTHER PUBLICATIONS

Treutlein et al., Reconstructing lineage hierarchies of the distal lung epithelium using single-cell RNA-seq, Nature 2014, 509, 371-375.
Trzupek et al., "Discovery of CD80 and CD86 as recent activation markers on regulatory T cells by protein-RNA single-cell analysis", Genome Medicine 2020, 12(1), in 22 pages.
Uellendahl-Werth et al., "A benchmark of hemoglobin blocking during library preparation for mRNA Sequencing of human blood samples," Scientific Reports 2020, 10(1), 5630.
Ullal et al., "Cancer cell profiling by barcoding allows multiplexed protein analysis in fine needle aspirates," Sci Transl Med. 2014, 6(219), 22 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vestheim et al., "Application of Blocking Oligonucleotides to Improve Signal-to-Noise Ratio in a PCR," Methods in Molecular Biology 2011, 687, 265-274.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Wang et al., "Tagmentation-based whole-genome bisulfite sequencing," Nature Protocols 2013, 8(10), 2022-2032.
Wangsanuwat et al., "Efficient and cost-effective bacterial mRNA sequencing from low input samples through ribosomal RNA depletion," BMC Genomics 2020, 21(1), 1-12.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Wu & Lambowitz, "Facile single-stranded DNA sequencing of human plasma DNA via thermostable group II intron reverse transcriptase template switching," Scientific Reports 2017, 7(8421), 1-14.
Yandell et al., "A probabilistic disease-gene finder for personal genomes," Genome Res. 2011, 21(9), 1529-1542.
Yang & Zhao, "Quantitative Analysis of Nonoxynol-9 in Blood," Contraception 1991, 43(2), 161-166.
Ye et al., "Fluorescent microsphere-based readout technology for multiplexed human single nucleotide polymorphism analysis and bacterial identification," Human Mutation 2001, 17(4), 305-316.
Yoon et al., "Sensitive and accurate detection of copy number variants using read depth of coverage," Genome Res. 2009, 19, 1586-1592.
Zeberg et al., "The major genetic risk factor for severe COVID-19 is inherited from Neanderthals," Nature 2020, 587(7835), 1-13.
Zagordi et al., "Error correction of next-generation sequencing data and reliable estimation of HIV quasispecies," Nucleic Acids Research 2010, 38(21), 7400-7409.
Zhang et al., "Immunoaffinity Purification of Plasma Membrane with Secondary Antibody Superparamagnetic Beads," Journal of Proteome 2006, 6, 34-43.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A Smart Approach for Full-Length cDNA Library Construction," BioTechniques 2001, 30(4), 892-897.
Examination Report dated Sep. 3, 2024 in Australian Patent Application No. 2019262048.
Examination Report dated Apr. 16, 2025 in European Patent Application No. 23166582.9.
Extended Search Report dated Oct. 4, 2023 in European Patent Application No. 23166582.9.
Final Office Action dated Sep. 19, 2024 in U.S. Appl. No. 18/324,890.
Office Action dated Aug. 10, 2024 in Chinese Patent Application No. 201980037175.0.
Office Action dated Mar. 31, 2025 in Japanese Patent Application No. 2023-213088.

\* cited by examiner gDNA fragments after transposition

RNA produced by in vitro transcription

HIGH THROUGHPUT MULTIOMICS SAMPLE ANALYSIS

RELATED APPLICATIONS

The present application is a continuation of U.S. patent application Ser. No. 16/400,885, filed on May 1, 2019, which claims priority under 35 U.S.C. § 119(e) to U.S. Provisional Application No. 62/666,483, filed May 3, 2018. The content of these related applications is expressly incorporated herein by reference in its entirety.

FIELD

The present disclosure relates generally to the field of molecular biology, and for particular to multiomics analysis of cells using molecular barcoding.

DESCRIPTION OF THE RELATED ART

Methods and techniques such as molecular barcoding are useful for single cell transcriptomics analysis, including deciphering gene expression profiles to determine the states of cells using, for example, reverse transcription, polymerase chain reaction (PCR) amplification, and next generation sequencing (NGS). Molecular barcoding is also useful for single cell proteomics analysis. There is a need for methods and techniques for multiomics analysis of single cells.

SUMMARY

Disclosed herein include embodiments of a method of sample analysis. For example, the sample analysis can comprise, consist essentially of, or consist of single cell analysis. In some embodiments, the method includes: contacting double-stranded deoxyribonucleic acid (dsDNA) (e.g., genomic DNA (gDNA)) from a cell, whether the gDNA is in the cell, an organelle of the cell such as the nucleus or a mitochondrion, or a cell fraction or extract during the contacting) with a transposome. The transposome can comprise a double-strand nuclease configured to induce a double-stranded DNA break at a structure comprising dsDNA (e.g., a transposase), and two copies of an adaptor having a 5' overhang comprising a capture sequence to generate a plurality of overhang dsDNA fragments each comprising two copies of the 5' overhangs. The method can comprise barcoding the plurality of overhang dsDNA fragments using a plurality of barcodes to generate a plurality of barcoded DNA fragments, wherein each of the plurality of barcodes comprises a cell label sequence, a molecular label sequence, and the capture sequence, wherein at least two of the plurality of barcodes comprise different molecular label sequences, and wherein at least two of the plurality of barcodes comprise an identical cell label sequence. The method can comprise detecting sequences of the plurality of barcoded DNA fragments. The method can comprise determining information relating the dsDNA sequences to the structure comprising dsDNA based on the sequences of the plurality of barcoded DNA fragments in the sequencing data. The method can further comprise contacting the plurality of overhang dsDNA fragments with a polymerase to generate a plurality of complementary dsDNA fragments each comprising a complementary sequence to at least a portion of the 5' overhang; and denaturing the plurality of complementary dsDNA fragments to generate a plurality of single stranded DNA (ssDNA) fragments, in which the ssDNA fragments are barcoded, thus barcoding the DNA fragments. In some embodiments, the dsDNA comprises, consists essentially of, or consists of gDNA. In any method of sample analysis as described herein, the transposome can target a specified structure comprising dsDNA, for example chromatin, a particular DNA methylation state, a DNA in a specified organelle, or the like. It is contemplated that the method of sample analysis can identify particular DNA sequences associated with structures targeted by the transposome, for example, chromatin-accessible DNA, construct DNA, organelle DNA, or the like.

In some embodiments, a method of sample analysis includes: generating a plurality of nucleic acid fragments from dsDNA (e.g., gDNA from a cell, whether the gDNA is in the cell, or the nucleus of the cell, during the contacting), wherein each of the plurality of nucleic acid fragments comprises a capture sequence, a complement of the capture sequence, a reverse complement of the capture sequence, or a combination thereof; barcoding the plurality of nucleic acid fragments using a plurality of barcodes to generate a plurality of barcoded DNA fragments, wherein each of the plurality of barcodes comprises a cell label sequence, a molecular label sequence, and the capture sequence, wherein at least two of the plurality of barcodes comprise different molecular label sequences, and wherein at least two of the plurality of barcodes comprise an identical cell label sequence; and detecting sequences of the plurality of barcoded DNA fragments. The method can further comprise determining information relating the dsDNA sequences to a structure comprising the dsDNA based on the sequences of the plurality of barcoded DNA fragments in the sequencing data.

In some embodiments, for any method of sample analysis described herein, generating the plurality of nucleic acid fragments can comprise: contacting the dsDNA with a transposome, in which the transposome comprises a double-strand nuclease configured to induce a double-stranded DNA break at a structure comprising dsDNA and two copies of an adaptor comprising the capture sequence, to generate a plurality of complementary dsDNA fragments each comprising a sequence complementary to the capture sequence. The double-strand nuclease can be loaded with the two copies of the adaptor. The method can further comprise denaturing the complementary dsDNA fragments to generate a plurality of single stranded DNA (ssDNA) fragments. The method can comprise barcoding the plurality of ssDNA fragments, thus generating the plurality of barcoded DNA fragments. The method can further comprise denaturing the barcoded DNA fragment to generate barcoded single-stranded DNA (ssDNA) fragments.

In some embodiments, for any method of sample analysis described herein, generating the plurality of nucleic acid fragments can comprise: contacting the dsDNA with a transposome, wherein the transposome comprises a double-strand nuclease configured to induce a double-stranded DNA break at a structure comprising dsDNA and two copies of an adaptor having a 5' overhang comprising a capture sequence, to generate a plurality of overhang dsDNA fragments each with two copies of the 5' overhangs; and contacting the plurality of overhang dsDNA fragments having the 5' overhangs with a polymerase to generate the plurality of complementary dsDNA fragments each comprising a complementary sequence to at least a portion of the 5' overhangs. The double-strand nuclease can be loaded with the two copies of the adaptor. The method can further comprise denaturing the complementary dsDNA fragments to generate a plurality of single stranded DNA (ssDNA)

fragments. The method can comprise barcoding the ssDNA fragments, thus generating the barcoded DNA. The method can further comprise denaturing the barcoded DNA fragment to generate barcoded single-stranded DNA (ssDNA) fragments. In some embodiments, for any method of sample analysis described herein, the barcoded DNA fragments can be ssDNA fragments.

In some embodiments, for any method of sample analysis described herein, none of the plurality of complementary dsDNA fragments comprises an overhang (e.g., a 3' overhang or a 5' overhang). In some embodiments, for any method of sample analysis described herein, the adaptor can comprise a DNA end sequence of the transposon. By way of example, the double-strand nuclease configured to induce a double-stranded DNA break at a structure comprising dsDNA can comprise a transposase, such as a Tn5 transposase. Examples of other suitable transposases are described herein. In some embodiments, for any method of sample analysis described herein, the plurality of complementary dsDNA fragments each comprise blunt ends.

In some embodiments, for any method of sample analysis described herein, generating the plurality of nucleic acid fragments comprises: fragmenting the dsDNA to generate a plurality of dsDNA fragments. Fragmenting the dsDNA can comprise contacting the dsDNA with a restriction enzyme to generate the plurality of dsDNA fragments each with one or two blunt ends. In some embodiments, at least one of the plurality of dsDNA fragments can comprise a blunt end. In some embodiments, at least one of the plurality of dsDNA fragments can comprise a 5' overhang and/or a 3' overhang. In some embodiments, none of the plurality of dsDNA fragments comprise a blunt end.

In some embodiments, for any method of sample analysis described herein, fragmenting the dsDNA can comprise contacting the dsDNA with a CRISPR associated protein (e.g., Cas9 or Cas12a) to generate the plurality of dsDNA fragments. By way of example, a guide RNA complementary to a target DNA motif or sequence can be used to target the CRISPR associated protein to generate double-stranded DNA breaks at the target DNA motif or sequence.

In some embodiments, for any method of sample analysis described herein, generating the plurality of nucleic acid fragments comprises: appending two copies of an adaptor comprising a sequence complementary to a capture sequence to at least one of the plurality of dsDNA fragments to generate a plurality of dsDNA fragments. For example, the adaptors can be appended by a transposase as described herein. For example, appending the two copies of the adaptor can comprise ligating the two copies of the adaptor to at least one of the plurality of dsDNA fragments to generate the plurality of dsDNA fragments comprising the adaptor.

In some embodiments, for any method of sample analysis described herein, the capture sequence comprises a poly(dT) region. The sequence complementary to the capture sequence can comprise a poly(dA) region.

In some embodiments, for any method of sample analysis described herein, fragmenting the dsDNA can comprise contacting the dsDNA with a restriction enzyme to generate the plurality of dsDNA fragments, wherein at least one of the plurality of dsDNA fragments comprises the capture sequence. The capture sequence can be complementary to the sequences of the 5' overhangs. The sequence complementary to the capture sequence can comprise the sequence of the 5' overhang. In some embodiments, the capture sequence comprises a sequence that does not comprise three, four, five, six, or more consecutive T's. For example, the capture sequence can comprise a sequence characteristic of one or both strands of the target dsDNA.

In some embodiments, for any method of sample analysis described herein, the dsDNA is inside an organelle of the cell, for example a nucleus. The method can include permeabilizing a nucleus to generate a permeabilized nucleus, for example using a detergent such as Triton X-100. The method can include fixing a cell comprising the nucleus prior to permeabilizing the nucleus. In some embodiments, for any method of sample analysis described herein, the dsDNA is inside at least one of a nucleus, a nucleolus, a mitochondrion, or a chloroplast. In some embodiments, the dsDNA is selected from the group consisting of: nuclear DNA (e.g., as a part of chromatin), nucleolar DNA, genomic DNA, mitochondrial DNA, chloroplast DNA, construct DNA, viral DNA, or a combination of two or more of the listed items. Examples of construct DNA can include plasmids, cloning vectors, expression vectors, hybrid vectors, minicircles, cosmids, viral vectors, BACs, YACs, and HACs. By way of example, viral DNA can be inserted into a host genome, of present in an extragenomic DNA. For example, a method of sample analysis as described herein can quantify DNA or a class of DNA in one or more organelles of a cell. For example, a method of sample analysis as described herein can quantify viral DNA or a viral load of DNA in a cell. For example, a method of sample analysis as described herein can quantify construct DNA in a cell (e.g., plasmids, cloning vectors, expression vectors, hybrid vectors, minicircles, cosmids, viral vectors, BACs, YACs, and/or HACs). Thus, it is contemplated that the method can yield information about transposome-accessible structures comprising the dsDNA.

In some embodiments, for any method of sample analysis described herein, the method comprises denaturing the plurality of nucleic acid fragments to generate a plurality of ssDNA fragments, wherein barcoding the plurality of nucleic acid fragments comprises barcoding the plurality of ssDNA fragments using the plurality of barcodes to generate the plurality of barcoded ssDNA fragments. In some embodiments, for any method of sample analysis described herein, the adaptor comprises a promoter sequence. Generating the plurality of nucleic acid fragments can comprise transcribing the plurality of dsDNA fragments using in vitro transcription to generate a plurality of ribonucleic acid (RNA) molecules, and wherein barcoding the plurality of nucleic acid fragments comprises barcoding the plurality of RNA molecules. The promoter sequence can comprise a T7 promoter sequence.

In some embodiments, for any method of sample analysis described herein, determining the information relating to the dsDNA (e.g., gDNA) comprises determining chromatin accessibility of the dsDNA (e.g., gDNA) based on the sequences and/or abundance of the plurality of barcoded DNA fragments in the sequencing data obtained. Determining the chromatin accessibility of the dsDNA can comprise: aligning the sequences of the plurality of barcoded DNA fragments to a reference sequence of the dsDNA (e.g., gDNA); identifying regions of the dsDNA corresponding the ends of barcoded DNA fragments (e.g., barcoded ssDNA fragments) of the plurality of ssDNA fragments to accessibility above a threshold. Determining the chromatin accessibility of the dsDNA (e.g., gDNA) can comprise: aligning the sequences of the plurality of barcoded DNA fragments (e.g., ssDNA fragments) to a reference sequence of the dsDNA (e.g., gDNA); and determining the accessibility of regions of the dsDNA (e.g., gDNA) corresponding the ends of barcoded DNA fragments (e.g., barcoded ssDNA fragments) of the plurality of barcoded DNA fragments (e.g., barcoded ssDNA fragments) based on the numbers of the barcoded DNA fragments (e.g., barcoded ssDNA fragments) of the plurality of barcoded DNA (e.g., barcoded ssDNA fragments) fragments in the sequencing data.

In some embodiments, for any method of sample analysis described herein, determining the information relating to the dsDNA (e.g., gDNA) comprises determining genome information of the dsDNA based on the sequences of the plurality of barcoded DNA fragments (e.g., barcoded ssDNA fragments) in the sequencing data obtained. The method of sample analysis can comprise digesting nucleosomes associated with the dsDNA. Determining the genome information of the dsDNA can comprise: determining at least a partial sequence of the dsDNA by aligning the sequences of the plurality of barcoded DNA fragments (e.g., barcoded ssDNA fragments) to a reference sequence of the dsDNA.

In some embodiments, for any method of sample analysis described herein, determining the information relating the dsDNA (e.g., gDNA) to the structure comprising dsDNA comprises determining methylome information of the dsDNA (e.g., gDNA) based on the sequences of the plurality of barcoded DNA fragments in the sequencing data obtained. The method of sample analysis can comprise digesting nucleosomes associated with the dsDNA. The method of sample analysis can comprise performing bisulfite conversion of cytosine bases of a plurality of single-stranded DNA fragments of the plurality of overhang DNA fragments or plurality of nucleic acid fragments (e.g., obtained by denaturing overhang DNA fragments or the plurality of nucleic acid fragments) to generate a plurality of bisulfite-converted ssDNA with uracil bases. Barcoding the plurality of overhang DNA fragments or barcoding the plurality of nucleic acid fragments can comprise barcoding the plurality of bisulfite-converted ssDNA using the plurality of barcodes to generate the plurality of barcoded ssDNA fragments. Determining the methylome information can comprise: determining a position of the plurality of barcoded DNA fragments (e.g., barcoded ssDNA fragments) in the sequencing data has a thymine base and the corresponding position in a reference sequence of the dsDNA has a cytosine base to determine the corresponding position in the dsDNA has a methylcytosine base.

In some embodiments, for any method of sample analysis described herein, the barcoding comprises: stochastically barcoding the plurality of DNA fragments (e.g., ssDNA fragments) or the plurality of nucleic acids using the plurality of barcodes to generate a plurality of stochastically barcoded DNA fragments. The barcoding can comprise: barcoding the plurality of DNA fragments (e.g., ssDNA fragments) or plurality of nucleic acid fragments using the plurality of barcodes associated with a particle to generate the plurality of barcoded ssDNA fragments, wherein the barcodes associated with the particle comprise an identical cell label sequence and at least 100 different molecular label sequences.

In some embodiments, for any method of sample analysis described herein, at least one barcode the plurality of barcodes can be immobilized on the particle. At least one barcode of the plurality of barcodes can partially immobilized on the particle. At least one barcode of the plurality of barcodes can be enclosed in the particle. At least one barcode of the plurality of barcodes can be partially enclosed in the particle. The particle can be disruptable. The particle can comprise a disruptable hydrogel particle. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. In some embodiments, for any method of sample analysis described herein, at least one barcode of the plurality of barcodes can be partitioned from the other barcodes. It is contemplated that the partitioning can comprise, for example, disposing the barcode on a solid support such as a particle as described herein, disposing the barcode in a droplet (e.g., a microdroplet) such as a hydrogel droplet, or in a well of a substrate, such as a microwell, or chamber of a fluidic device (e.g., a microfluidic device).

In some embodiments, for any method of sample analysis described herein, the barcodes of the particle can comprise molecular labels with at least 1000 different molecular label sequences. The barcodes of the particle can comprise molecular labels with at least 10000 different molecular label sequences. The molecular labels of the barcodes can comprise random sequences. The particle can comprise at least 10000 barcodes.

In any of the methods of single cell analysis described herein, barcoding the plurality of overhang DNA fragments or plurality of nucleic acid fragments can comprise: contacting a plurality of ssDNAs (of the DNA fragments or nucleic acid fragments) with the capture sequence of the plurality of barcodes; and transcribing the plurality ssDNA using the plurality of barcodes to generate the plurality of barcoded ssDNA fragments. The method of sample analysis can include: prior to obtaining the sequencing data of the plurality of barcoded ssDNA fragments, amplifying the plurality of barcoded ssDNA fragments to generate a plurality of amplified barcoded DNA fragments. Amplifying the plurality of barcoded ssDNA fragments can comprise: amplifying the barcoded ssDNA fragments by polymerase chain reaction (PCR).

In some embodiments, any method of sample analysis described herein can include: barcoding a plurality of targets of the nucleus using the plurality of barcodes to generate a plurality of barcoded targets; and obtaining sequencing data of the barcoded targets.

In some embodiments, for any of the methods of sample analysis described herein, the dsDNA from the cell is selected from the group consisting of: nuclear DNA, nucleolar DNA, genomic DNA, mitochondrial DNA, chloroplast DNA, construct DNA, viral DNA, or a combination of two or more of the listed items. In some embodiments, for any of the methods of sample analysis described herein, the 5' overhangs comprise poly dT sequences. In some embodiments, for any of the methods of sample analysis described herein, the method further comprises capturing a ssDNA fragment of the plurality of barcoded sDNA fragments on a particle comprising an oligonucleotide comprising the capture sequence, the cell label sequence, and the molecular label sequence, wherein the capture sequence comprises a poly dT sequence that binds to a poly A tail on the ssDNA fragment, said captured ssDNA fragment comprising a methylated cytidine, performing a bisulfide conversion reaction on the ssDNA fragment to convert the methylated cytidine to a thymidine, extending the ssDNA fragment in the 5' to 3' direction to produce the barcoded ssDNA fragment comprising the thymidine, the barcoded ssDNA comprising the capture sequence, molecular label sequence, and cell label sequence, extending the oligonucleotide in the 5' to 3' direction using a reverse transcriptase or polymerase or combination thereof to produce a complementary DNA strand complementary to the barcoded ssDNA comprising the thymidine, denaturing the barcoded ssDNA and complementary DNA strand to produce single stranded sequences, and amplifying the single stranded sequences. The method can further comprise determining whether a position of the plurality ssDNA fragments in the sequencing data has a thymine base and the corresponding position in a reference sequence of the dsDNA has a cytosine base, comprising, after the bisulfide conversion reaction, determining the corresponding position of the thymine base in the reference sequence to be a cytosine base.

In some embodiments, for any of the methods of sample analysis described herein, the double-strand nuclease of the transposome is selected from the group consisting of a transposase, a restriction endonuclease, a CRISPR associated protein, a duplex-specific nuclease, or a combination of these. In some embodiments, for any of the methods of sample analysis described herein, the transposome further comprises an antibody or fragment thereof, apatmer, or DNA binding domain that binds to the structure comprising dsDNA. In some embodiments, for any of the methods of sample analysis described herein, the transposome further comprises a ligase.

In some embodiments, a nucleic acid reagent is described. The nucleic acid reagent can comprise a capture sequence, a barcode, a primer binding site, and a double-stranded DNA-binding agent. The capture sequence may comprise a poly(A) region. The primer binding site may comprise a universal primer binding site. The nucleic acid reagent can be plasma-membrane impermeable. In some embodiments, the nucleic acid reagent is configured to specifically bind to dead cells. In some embodiments, the nucleic acid reagent does not bind to live cells.

In some embodiments, for any of the methods of sample analysis described herein, the method further comprises contacting a cell with a nucleic acid reagent. The nucleic acid reagent can be as described herein. The nucleic acid reagent can comprise a capture sequence, a barcode, a primer binding site; and a double-stranded DNA-binding agent. The cell can be a dead cell, and the nucleic acid binding reagent can bind to double-stranded DNA in the dead cell. The method can comprise washing the dead cell to remove excess of the nucleic acid binding reagent. The method can comprise lysing the dead cell. The lysing can release the nucleic acid binding reagent. The method can comprise barcoding the nucleic acid binding reagent. In the method of some embodiments, the cell is associated with a solid support comprising an oligonucleotide comprising a cell label sequence, barcoding comprises barcoding the nucleic acid binding reagent with the cell label sequence. The solid support can comprise a plurality of the oligonucleotides, each comprising the cell label sequence and a different molecular label sequence. In some embodiments, the method further comprises sequencing the barcoded nucleic acid binding reagents, and determining a presence of a dead cell based on the presence of the barcode of the nucleic acid reagent. In some embodiments, the method further comprises associating two or more cells each with different solid supports comprising different cell labels, whereby each of the two or more cells is associated one-to-one with a different cell label. In some embodiments, the method further comprises determining a number of dead cells in the sample based on the number of unique the cell labels associated with a barcode of a nucleic acid reagent. Determining the number of molecular label sequences with distinct sequences associated with the cell label and the control barcode sequence can comprise determining the number of molecular label sequences with the highest number of distinct sequences associated with the cell label and the control barcode sequence for each cell label in the sequencing data. In the method of some embodiments, the nucleic acid binding reagent does not enter a live cell, and thus does not bind to double-stranded DNA in the live cell. In some embodiments, the method further comprises contacting a dead cell with a protein binding reagent associated with a unique identifier oligonucleotide, in which the protein binding reagent binds to a protein of the dead cell; and barcoding the unique identifier oligonucleotide. In the method of some embodiments, the protein binding reagent comprises an antibody, a tetramer, an aptamer, a protein scaffold, an invasin, or a combination thereof. In the method of some embodiments, a protein target of the protein binding reagent is selected from a group comprising 10-100 different protein targets, or a cellular component target of the cellular component binding reagent is selected from a group comprising 10-100 different cellular component targets. In the method of some embodiments, a protein target of the protein binding reagent comprises a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In the method of some embodiments, the protein binding reagent comprises an antibody or fragment thereof that binds to a cell surface protein. In the method of some embodiments, the barcoding is with a barcode comprising a molecular label sequence.

Some embodiments include a method of sample analysis. The method can comprise contacting a dead cell of a sample with a nucleic acid binding reagent, a nucleic acid binding reagent comprising a capture sequence, a barcode, a primer binding site, and a double-stranded DNA-binding agent. The nucleic binding reagent can bind to double-stranded DNA in the dead cell. The method can comprise washing excess nucleic acid binding reagent from the dead cell. The method can comprise lysing the dead cell, thus releasing the nucleic acid binding reagent from the dead cell. The method can comprise barcoding the nucleic acid binding reagent. In the method of some embodiments, barcoding comprises capturing the dead cell on a solid support, such as a bead, the solid support comprising a cell label sequence and a molecular label sequence. In some embodiments, the method further comprises determining a number of distinct molecular label sequences associated with each cell label sequence, and determining a number of dead cells in the sample based on the number of distinct cell label sequences associated with molecular label sequences. In the method of some embodiments, determining the number of molecular label sequences with distinct sequences associated with the cell label and the control barcode sequence comprises determining the number of molecular label sequences with the highest number of distinct sequences associated with the cell label for each cell label in the sequencing data. In some embodiments, the method further comprises contacting a dead cell with a protein binding reagent associated with a unique identifier oligonucleotide. The protein binding reagent can bind to a protein of the dead cell. The method can further comprise barcoding the unique identifier oligonucleotide. In the method of some embodiments, the protein binding reagent is associated with two or more sample indexing oligonucleotides with an identical sequence. In the method of some embodiments, the protein binding reagent is associated with two or more sample indexing oligonucleotides with different sample indexing sequences. In the method of some embodiments, the protein binding reagent comprises an antibody, a tetramer, an aptamer, a protein scaffold, an invasin, or a combination thereof. In the method of some embodiments, a protein target of the protein binding reagent is selected from a group comprising 10-100 different protein targets, or wherein a cellular component target of the cellular component binding reagent is selected from a group comprising 10-100 different cellular component targets. In the method of some embodiments, a protein target of the protein binding reagent comprises a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In the method of some embodiments, the protein binding reagent comprises an antibody or fragment thereof that binds to a cell surface protein.

In the method of some embodiments, the capture sequence and the sequence complementary to the capture sequence are a specified pair of complementary nucleic acids of at least 5 nucleotides to about 25 nucleotides in length.

In some embodiments, a method of sample analysis is described. The method can comprise contacting double-stranded deoxyribonucleic acid (dsDNA) from a cell with a transposome, wherein the transposome comprises a double-strand nuclease configured to induce a double-stranded DNA break at a structure comprising dsDNA and two copies of an adaptor having a 5' overhang comprising a capture sequence to generate a plurality of overhang dsDNA fragments each comprising two copies of the 5' overhangs. The method can comprise contacting the plurality of overhang dsDNA fragments with a polymerase to generate a plurality of complementary dsDNA fragments each comprising a complementary sequence to at least a portion of each of the 5' overhang. The method can comprise denaturing the plurality of complementary dsDNA fragments to generate a plurality of single-stranded DNA (ssDNA) fragments. The method can comprise barcoding the plurality of ssDNA fragments using a plurality of barcodes to generate a plurality of barcoded ssDNA fragments, wherein each of the plurality of barcodes comprises a cell label sequence, a molecular label sequence, and the capture sequence, wherein at least two of the plurality of barcodes comprise different molecular label sequences, and wherein if the plurality of barcodes comprise an identical cell label sequence. The method can comprise obtaining sequencing data of the plurality of barcoded ssDNA fragments. The method can comprise quantifying a quantity of the dsDNA in the cell based on a quantity of unique molecular label sequences associated with the same cell label sequence. In some embodiments, the method further comprises capturing a ssDNA fragment of the plurality of ssDNA fragments on a solid support comprising an oligonucleotide comprising the capture sequence, the cell label sequence, and the molecular label sequence, wherein the capture sequence comprises a poly dT sequence that binds to a poly A tail on the ssDNA fragment; extending the ssDNA fragment in the 5' to 3' direction to produce the barcoded ssDNA fragment, the barcoded ssDNA comprising the capture sequence, molecular label sequence, and cell label sequence; extending the oligonucleotide in the 5' to 3' direction using a reverse transcriptase or polymerase or combination thereof to produce a complementary DNA strand complementary to the barcoded ssDNA; denaturing the barcoded ssDNA and complementary DNA strand to produce single stranded sequences; and amplifying the single stranded sequences. In some embodiments, the method further comprising a bisulfite conversion of cytosine bases of the plurality of ssDNA fragments to generate a plurality of bisulfite-converted ssDNA fragments comprising uracil bases.

In any of the methods described herein, the dsDNA can comprise construct DNA. The construct DNA can be selected from the group consisting of plasmids, cloning vectors, expression vectors, hybrid vectors, minicircles, cosmids, viral vectors, BACs, YACs, and HACs. In some embodiments, the number of construct DNA ranges from 1 to about $1 \times 10^6$.

In any of the methods described herein, the dsDNA can comprise viral DNA. The load of viral DNA in the cell can range from about $1 \times 10^2$-$1 \times 10^6$.

In some embodiments, a kit for sample analysis is described. The kit can comprise a transposome as described herein, and a plurality of barcodes as described herein. Each transposome can comprise a double-strand nuclease configured to induce a double-stranded DNA break at a structure comprising dsDNA (e.g., a transposase as described herein) and two copies of an adaptor having a 5' overhang comprising a capture sequence. Optionally, the transposome further comprises a ligase. Each barcode can comprise a cell label sequence, a molecular label sequence, and the capture sequence, for example a polyT sequence. At least two of the plurality of barcodes comprise different molecular label sequences, and at least two of the plurality of barcodes comprise an identical cell label sequence. For example, the barcodes can comprise at least 10, 50, 100, 500, 1000, 5000, 10000, 50000, or 100000 different molecular labels. The barcodes can be immobilized on particles as described herein. All of the barcodes on the same particle can comprise the same cell label. In the kit of some embodiments, the barcodes are partitioned in wells of a substrate. All of the barcodes partitioned in each well can comprise the same cell label sequence, and wherein different wells comprise different cell label sequences.

DETAILED DESCRIPTION

Figure 1:
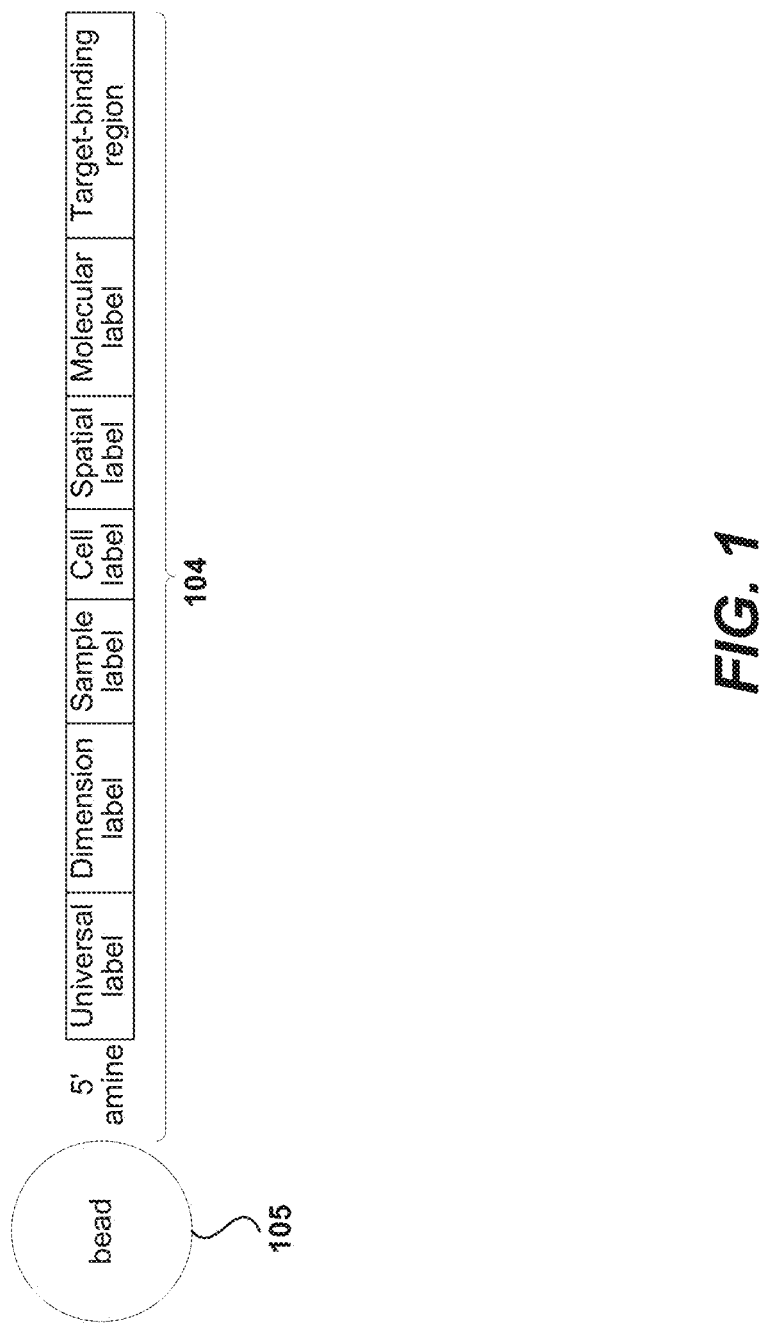
FIG. 1 illustrates a non-limiting exemplary barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Barcodes, such as stochastic barcodes, with molecular labels (also referred to as molecular indexes (MIs)) having different molecular label differences can be used to determine the abundance of nucleic acid targets, such as relative or absolute abundance of the nucleic acid targets. Stochastic barcoding can be performed using the Precise™ assay (Cellular Research, Inc. (Palo Alto, CA)) and the Rhapsody™ assay (Becton, Dickinson and Company (Franklin Lakes, NJ)). The Precise™ assay, or the Rhapsody™ assay, can utilize a non-depleting pool of stochastic barcodes with a large number, for example 6561 to 65536, unique molecular label sequences on poly(T) oligonucleotides to hybridize to all poly(A)-mRNAs in a sample during the reverse transcription (RT) step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular label sequences, and the numbers of mRNA molecules.

Disclosed herein include embodiments of a method of sample analysis. For example, any of the methods of sample analysis described herein can comprise, consist of, or consist essentially of single cell analysis. The method of sample analysis can be used for multiomics analysis using molecular barcoding (such as the Precise™ assay and Rhapsody™ assay. In some embodiments, the method of sample analysis includes: contacting double-stranded deoxyribonucleic acid (dsDNA) with a transposome, wherein the transposome comprises a double-strand nuclease configured to induce a double-stranded DNA break at a structure comprising dsDNA, and two copies of an adaptor having a 5' overhang comprising a capture sequence to generate a plurality of overhang double-stranded DNA (dsDNA) fragments each with two copies of the 5' overhangs. The double-stranded nuclease (e.g., a transposase) can be loaded with the two copies of the adaptor. The method can comprise contacting the plurality of overhang dsDNA fragments (comprising the 5' overhangs) with a polymerase to generate a plurality of complementary dsDNA fragments each comprising a complementary sequence to at least a portion of the 5' overhang; denaturing the plurality of complementary dsDNA fragments (each comprising the complementary sequence to at least a portion of the 5' overhang) to generate a plurality of single-stranded DNA (ssDNA) fragments; barcoding the plurality of ssDNA fragments using a plurality of barcodes to generate a plurality of barcoded ssDNA fragments, wherein each of the plurality of barcodes comprises a cell label sequence, a molecular label sequence, and the capture sequence, wherein at least two of the plurality of barcodes comprise different molecular label sequences, and wherein at least two of the plurality of barcodes comprise an identical cell label sequence; obtaining sequencing data of the plurality of barcoded ssDNA fragments; and determining information relating to the dsDNA (e.g., gDNA) based on the sequences of the plurality ssDNA fragments in the sequencing data obtained.

In some embodiments, for any method of sample analysis described herein, a double-stranded DNA can comprise, consist essentially of, or consist of any double-stranded DNA for example genomic DNA (gDNA), organelle DNA (e.g., nuclear DNA, nucleolar DNA, genomic DNA, mitochondrial DNA, and chloroplast DNA), viral DNA, and/or construct DNA (e.g., plasmids, cloning vectors, expression vectors, hybrid vectors, minicircles, cosmids, viral vectors, and/or artificial chromosomes such as BACs, YACs, and HACs).

In some embodiments, for any method of sample analysis described herein, construct DNA is selected from the group consisting of plasmids, cloning vectors, expression vectors, hybrid vectors, minicircles, cosmids, viral vectors, BACs, YACs, and HACs, or a combination of two or more of any of the listed items.

In some embodiments, for any method of sample analysis described herein, the number of construct DNA ranges from 1 to about $1 \times 10^6$.

In some embodiments, for any method of sample analysis described herein, a load of viral DNA ranges from about $1 \times 10^2$-$1 \times 10^6$.

A number of suitable double-stranded DNA binding reagents can be used in nucleic acid reagents and methods of sample analysis as described herein. In some embodiments, for any nucleic acid reagent and/or method of sample analysis described herein, a double-stranded DNA acid binding reagent is selected, without limitations, from the group consisting of anthracyclines (e.g., aclarubicin, aldoxorubicin, amrubicin, annamycin, bohemic acid, carubicin, cosmomycin B, daunorubicin, doxorubicin, epirubicin, idarubicin, menogaril, nogalamycin, pirarubicin, sabarubicin, valrubicin, zoptarelin doxorubicin, and zorubicin), amikhelline, 9-aminoacridine, 7-aminoactinomycin D, amsacrine, dactinomycin, daunorubicin, doxorubicin, ellipticine, ethidium bromide, mitoxantrone, pirarubicin, pixantrone, proflavine, and psoralen, or a combination of two or more of the listed items.

In some embodiments, any of the methods of sample analysis described herein includes: generating a plurality of nucleic acid fragments from double-stranded deoxyribonucleic acid (dsDNA) of a cell, wherein each of the plurality of nucleic acid fragments comprises a capture sequence, a complement of the capture sequence, a reverse complement of the capture sequence, or a combination thereof; barcoding the plurality of nucleic acid fragments using the plurality of barcodes to generate a plurality of barcoded single-stranded deoxyribonucleic acid (ssDNA) fragments, wherein each of the plurality of barcodes comprises a cell label sequence, a molecular label sequence, and the capture sequence, wherein at least two of the plurality of barcodes comprise different molecular label sequences, and wherein at least two of the plurality of barcodes comprise an identical cell label sequence; obtaining sequencing data of the plurality of barcoded ssDNA fragments; and determining information relating to the dsDNA based on the sequences of the plurality ssDNA fragments in the sequencing data obtained.

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, information on the following terms is provided below.

As used herein, the term "adaptor" has its customary and ordinary meaning in the art in view of this specification. It refers to a sequence to facilitate amplification, sequencing, and/or capture of associated nucleic acids. The associated nucleic acids can comprise target nucleic acids. The associated nucleic acids can comprise one or more of spatial labels, target labels, sample labels, indexing label, or barcode sequences (e.g., molecular labels). The adapters can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" has its customary and ordinary meaning in the art in view of this specification. It can refer two or more species that are identifiable as being co-located at a point in time. An association can refer to two or more species that are or were within a similar container. An association can refer to an informatics association. For example, digital information regarding two or more species can be stored and can be used to determine that one or more of the species were co-located at a point in time. An association can also refer to a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may refer to a covalent bond between a target and a label. An association can comprise hybridization between two molecules (such as a target molecule and a label).

As used herein, the term "complementary" has its customary and ordinary meaning in the art in view of this specification. It can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, a "complementary" sequence can refer to a "complement" or a "reverse complement" of a sequence. It is understood from the disclosure that if a molecule can hybridize to another molecule it may be complementary, or partially complementary, to the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" have their customary and ordinary meanings in the art in view of this specification. They can refer to nucleic acid codes associated with a target within a sample. A label can comprise, consist essentially of, or consist of, for example, a nucleic acid label. A label can be an entirely or partially amplifiable label. A label can be entirely or partially sequenceable label. A label can be a portion of a native nucleic acid that is identifiable as distinct. A label can comprise, consist essentially of, or consist of a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" has its customary and ordinary meaning in the art in view of this specification. It refers to a polynucleotide sequence, or fragment thereof. A nucleic acid can comprise, consist essentially of, or consist of nucleotides. A nucleic acid can be exogenous or endogenous to a cell. A nucleic acid can exist in a cell-free environment. A nucleic acid can comprise, consist essentially of, or consist of a gene or fragment thereof. A nucleic acid can comprise, consist essentially of, or consist of DNA. A nucleic acid can comprise, consist essentially of, or consist of RNA. A nucleic acid can comprise, consist essentially of, or consist of one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3' 5' linkages, 2' 5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise, consist essentially of, or consist of a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise, consist essentially of, or consist of a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise, consist essentially of, or consist of linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene (—$CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms. In some embodiments, the sample comprises, consists essentially of, or consists of a single cell. In some embodiments, the sample comprises, consists essentially of, or consists of at least 100,000, 200,000, 300,000, 500,000, 800,000, or 1,000,000 single cells.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" has its customary and ordinary meaning in the art in view of this specification. It can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead." It is contemplated that for any embodiments herein in which the barcode is immobilized on a solid support, particle, bead, or the like, the barcode can also be partitioned, for example in a droplet (e.g., a microdroplet) such as a hydrogel droplet, or in a well of a substrate, such as a microwell, or chamber of a fluidic device (e.g., a microfluidic device). Accordingly, wherever grouping, sorting, or partitioning nucleic acids by way of a "solid support" (e.g., a bead) is disclosed herein, partitioning in a fluid (for example, a droplet, such as microdroplet) or physical space, for example a microwell (e.g., on a multi-well plate) or a chamber (e.g., in a fluidic device) is also expressly contemplated.

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" has its customary and ordinary meaning in the art in view of this specification. It can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" has its customary and ordinary meaning in the art in view of this specification. It can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, US 2015/0299784, WO 2015/031691, and Fu et al, Proc Natl Acad Sci U.S.A. 2011 May 31; 108(22):9026-31 (the content of each of these publications is incorporated by reference in its entirety herein). In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 105. The barcode can comprise a universal label, a dimension label, a spatial label, a cell label, and/or a molecular label. The barcode can comprise a universal label, a cell label, and a molecular label. The barcode can comprise a universal label, a spatial label, a cell label, and a molecular label. The barcode can comprise a universal label, a dimensional label, a cell label, and a molecular label. The order of different labels (including but not limited to the universal label, the dimension label, the spatial label, the cell label, and/or the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo(dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., A well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead). In some embodiments, the unique molecular label sequence is partially or entirely encompassed by a particle (e.g., a hydrogel bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For barcoding (e.g. stochastic barcoding) using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. In some embodiments, a target-binding region does not comprise an oligo(dT). A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be disruptable (e.g., dissolvable or degradable). For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
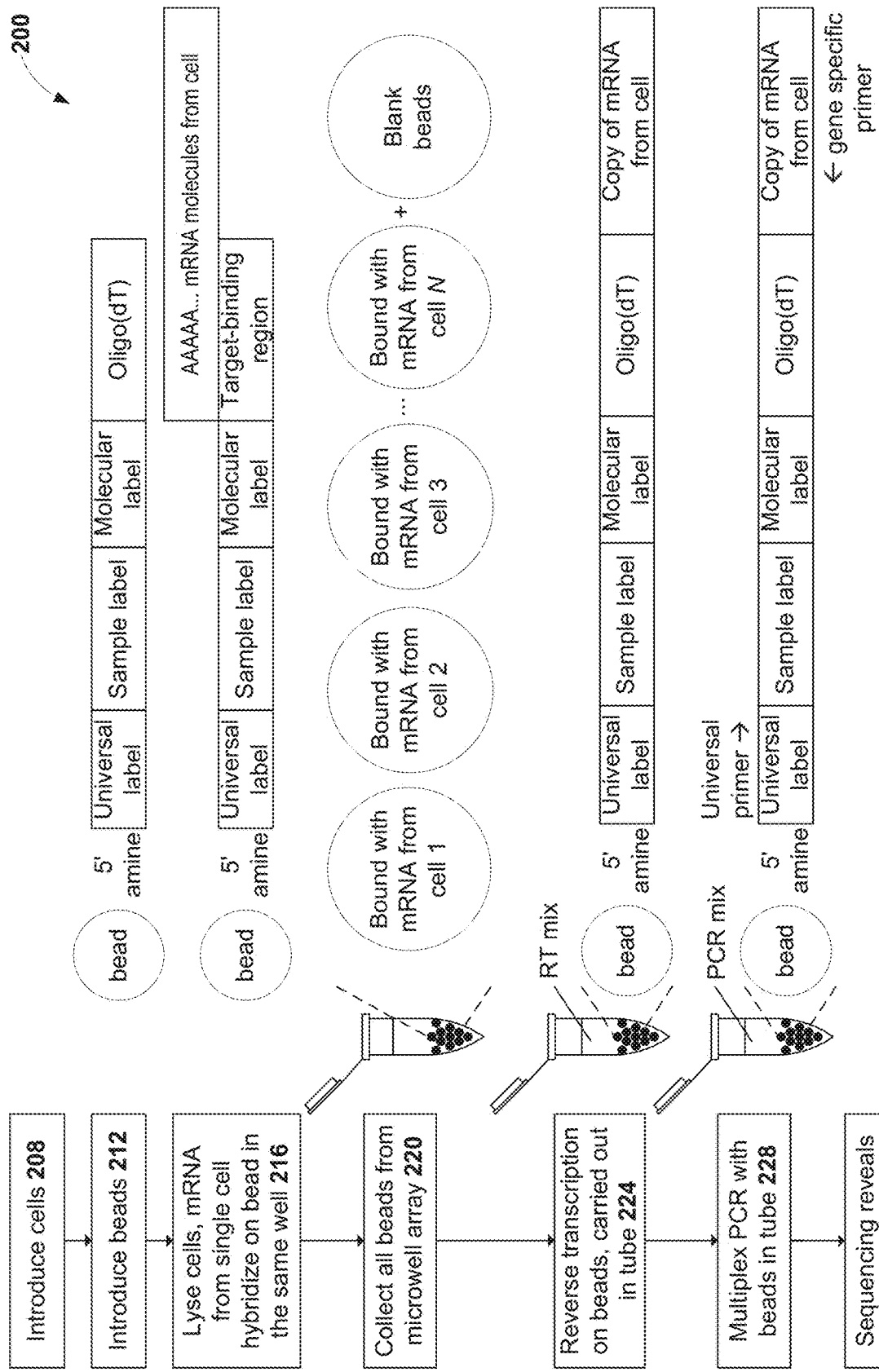
FIG. 2 shows a non-limiting exemplary workflow of barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate. In some embodiments, the barcodes can be associated with single cells in partitions, for example droplets such as microdroplets, or wells of a substrate such as microwells (e.g., on a multi-well plate) or chambers (e.g., in a fluidic device). Example droplets can include hydrogel droplets. The barcodes in the partitions can be immobilized on a solid support, or they can be free in solution.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. In some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease (which may also be referred to herein as "restriction enzyme") digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids described herein can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
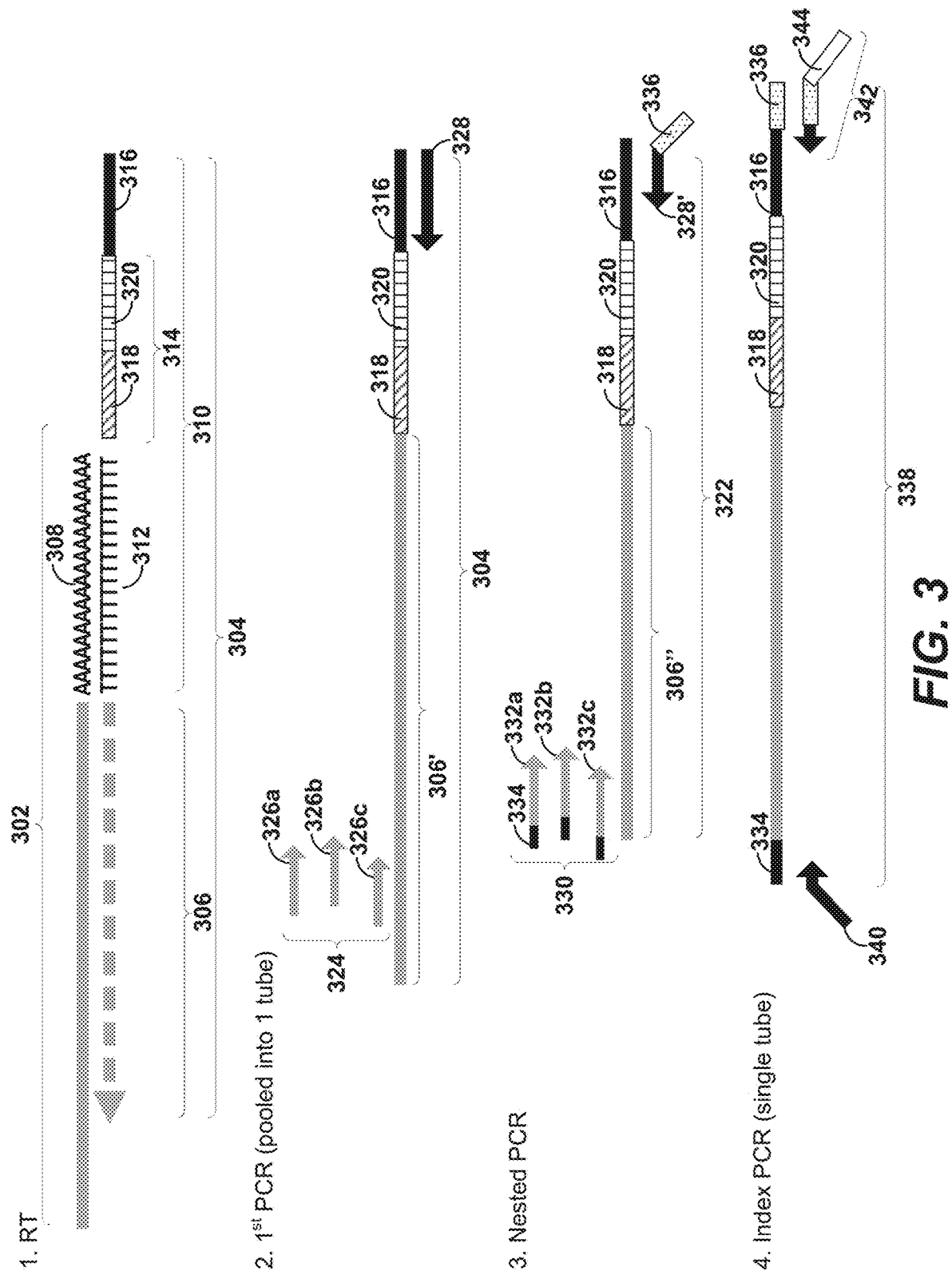
FIG. 3 is a schematic illustration showing a non-limiting exemplary process for generating an indexed library of the barcoded targets from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label sequence, a cell label sequence, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label sequence can include 3 to 20 nucleotides. In some embodiments, the molecular label sequence can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Multiomics Analysis

Disclosed herein include embodiments of a method for high throughput sample analysis. The method can be used with any sample analysis platform or system for partitioning single cells with single particles, such as platforms and systems based on droplets (e.g., Chromium™ Single Cell 3' Solution (10× Genomics (San Francisco, CA))), microwells (e.g., Rhapsody™ assay (Becton, Dickinson and Company (Franklin Lakes, NJ))), microfluidic chambers, and patterned substrates. The method can capture multiomics information, including genome, genomic accessibility (e.g., chromatin accessibility), and methylome. The method can be used with methods for transcriptomics analysis, proteomics analysis, and/or sample tracking. Using barcoding for proteomics analysis has been described in U.S. application Ser. No. 15/715,028, published as US 2018/0088112, the content of which is incorporated herein by reference in its entirety. Using barcoding for sample tracking has been described in U.S. application Ser. No. 15/937,713, published as US 2018/0346970, the content of which is incorporated herein by reference in its entirety. In some embodiments, multiomics information, such as genomics, chromatin accessibility, methylomics, transcriptomics, and proteomics, of single cells can be obtained using barcoding.

In some embodiments, the method includes appending a sequence complementary to that of the capture probes with cell and molecular labels or indices at the end of the genomic DNA fragments. For example, a poly(dA) tail (or any sequence) can be added to genomic fragments such that they can be captured by oligo(dT) probes (or a complementary sequence to the sequence added) flanked with cell and molecular barcodes. The method can be used to capture all, or part, of the following from single cells in a high throughput manner, including genome, methylome, chromatin accessibility, transcriptome, and proteome.

The method can include sample preparation before loading cellular materials onto any of these sample analysis systems. For example, utilizing enzymatic cutters, for example double-strand nucleases as described herein (such as transposase, restriction enzymes, and CRISPR associated proteins), dsDNA (e.g., gDNA) can be fragmented into genomic fragments within fixed cells or nuclei. A restriction enzyme can be used for high throughput multiomics sample analysis. For example, the method can include incubating cells with a restriction enzymes (followed by removing the restriction enzyme, for example). As another example, the method can include incubating cells with a ligase and adaptors with poly(dT)/poly(dA) or poly(dT)/poly(dA) with T7 promoter sequences flanked with the restriction sequence. As yet another example, the capture probe can have a sequence of the restriction site. In this embodiment, addition of dTs/dAs adaptors may not be needed. In some embodiments, Cas9/CRISPR can be used to cut at specified locations of the genome.

The cells or nuclei can be fresh or fixed (e.g., cells fixated with fixatives, such as aldehydes, oxidizing agents, hepesglutamic acid buffer-mediated organic solvent protection effect (HOPE) fixatives). In some embodiments, the method comprises contacting the cells with a nucleic acid reagent as described herein. The cells can then be washed so as to remove excess nucleic acid reagent. As described herein, the nucleic acid reagent can bind to dsDNA in dead cells, but not live cells, so that only dead cells will remain labeled with the nucleic acid reagent after the washing. In some embodiments, a sequence complementary to the capture probes (e.g., barcodes such as stochastic barcodes) is then appended to each end of the genomic fragments. The capture probes can be anchored on a solid support or in solution. The capture probe of a single cell transcriptomic analysis system can be a poly(dT) sequence. Thus, each end of the genomic fragments can be appended with a poly(dA) sequence. The cells or nuclei can then be heated or exposed to chemical to denature the double stranded genomic fragments appended with a poly(dA) sequence on each end is then loaded onto a sample analysis system. Upon cell and/or nucleus lysis, the genomic fragments with the appended sequence can be captured by the capture probes present, just like mRNA molecules with poly(A) tails can be captured by poly(dT) sequences of capture probes. Reverse transcriptase and/or DNA polymerase can be added to copy (e.g., reverse transcribe) the genomic fragments and append the cell and molecular labels or indices to the genomic fragments.

Figure 4A:
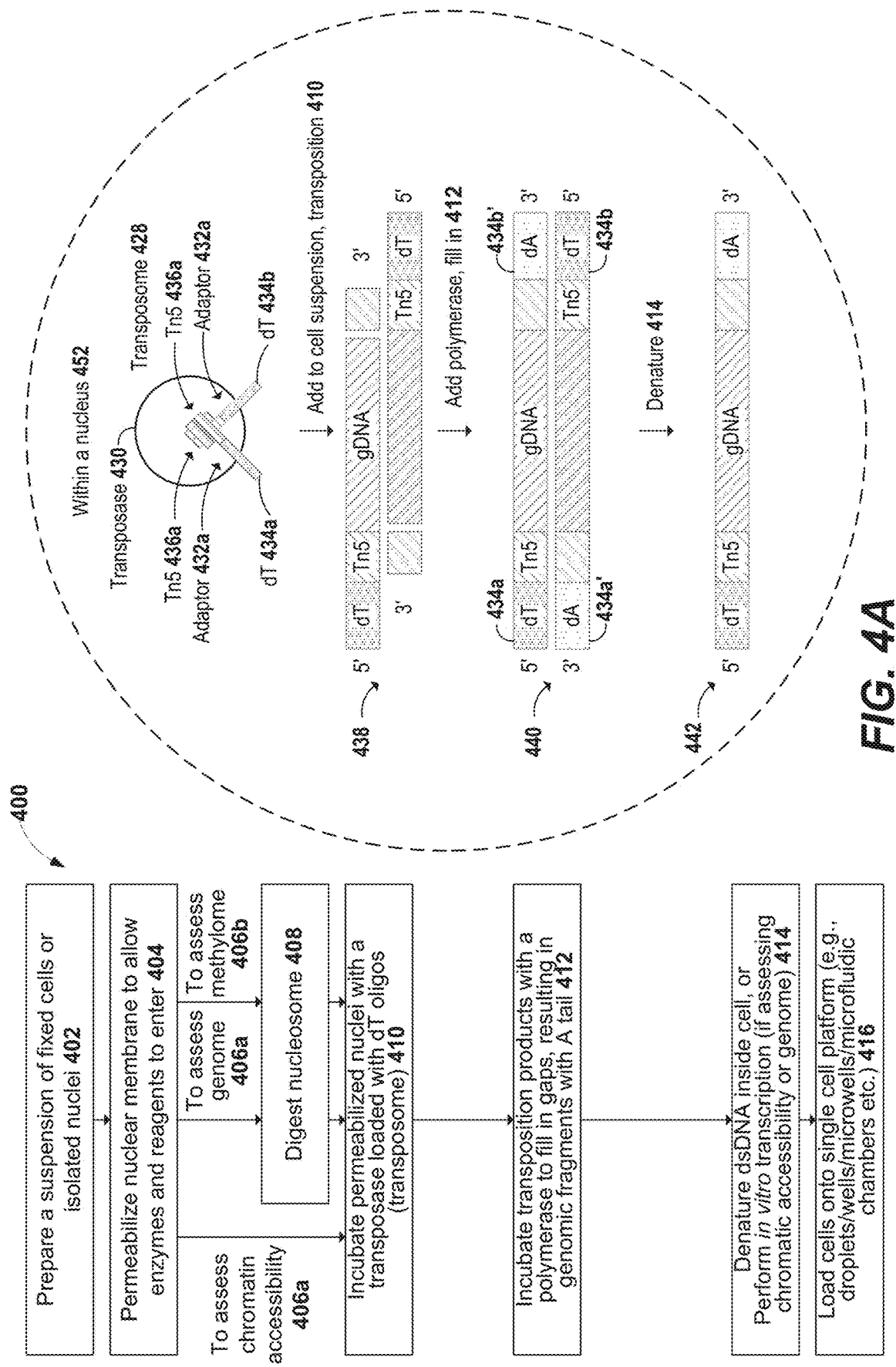
FIGS. 4A-4B show a schematic illustration of non-limiting exemplary methods of high throughput capturing of multiomics information from single cells.
Figure 4B:
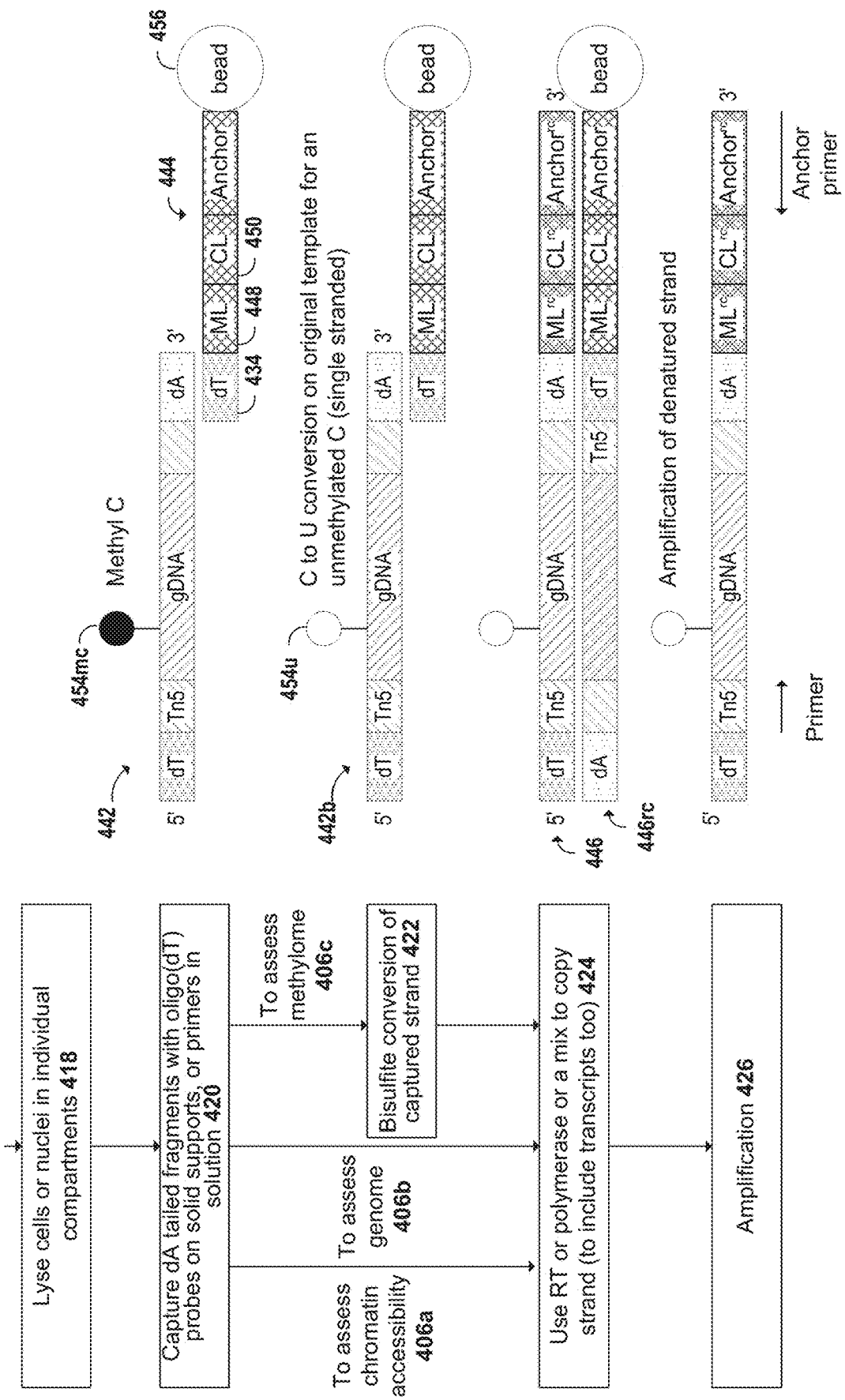

Disclosed herein include embodiments of a method of sample analysis. FIGS. 4A-4B show a schematic illustration of non-limiting exemplary embodiments of a method 400 of high throughput capturing of multiomics information from single cells. In some embodiments, the method 400 includes using a transposome to generate double-stranded DNA fragments with 5' overhangs (or 3' overhangs) comprising a capture sequence. The method 400 can include: contacting 410 double-stranded deoxyribonucleic acid (dsDNA), e.g., a genomic DNA (gDNA), with a transposome 428. The transposome 428 can comprise a double-strand nuclease configured to induce a double-stranded DNA break at a structure comprising dsDNA 430 and two copies 432a, 432b of an adaptor having a 5' overhang comprising a capture sequence (e.g., a poly(dT) sequence 434a, 434b). The double-strand nuclease 430 can be loaded with the two copies 432a and 432b of the adaptor 434a, 434b. Each copy 436a, 436b of the adaptor can comprise a DNA end sequence of the transposon (e.g., a Tn5 sequence 436a, 436b, or a sub-sequence thereof). The double-strand nuclease can be, or comprise, a transposase such as Tn5 transposase. Contacting 410 dsDNA (e.g., gDNA) with a transposome 428 can generate a plurality of overhang dsDNA fragments 438 each with two copies 432a, 432b of the 5' overhangs 434a, 434b.

In some embodiments, the method 400 includes contacting (e.g., at block 412) the plurality of overhang dsDNA fragments (with the 5' overhangs) 438 with a polymerase to generate a plurality of complementary dsDNA fragments each comprising a complementary sequence 434a', 434b' to at least a portion of the 5' overhang 434a, 434b. The method 400 can include denaturing (e.g., at block 414) the plurality of complementary dsDNA fragments 440 each comprising the complementary sequence to at least a portion of the 5' overhang to generate a plurality of single-stranded DNA (ssDNA) fragments 442, and barcoding (e.g., at block 424) the plurality of ssDNA fragments using a plurality of barcodes 444 to generate a plurality of barcoded ssDNA fragments (e.g., barcoded ssDNA fragments 446 or a complementary sequence thereof). At least some (e.g., at least 1, 2, 3, 4, 5, 6, 7, 8, 10, 100, 1000, 10000, 100000, 1000000, 10000000, or more) of the plurality of barcodes 444 comprise a cell label 448, a molecular label 450, and the capture sequence 434. Molecular labels 448 of at least two barcodes of the plurality of barcodes 444 can comprise with different molecular label sequences. At least two barcodes of the plurality of barcodes 444 can comprise cell labels 450 with an identical cell label sequence. The method 400 can include obtaining sequencing data of the plurality of barcoded ssDNA fragments 446 (or a complementary sequence thereof), and determining information relating to the dsDNA (e.g., gDNA) based on the sequences of the plurality ssDNA fragments 446 (or a complementary sequence thereof) in the sequencing data obtained.

The method 400 can include using a transposome 428 (which can comprise, e.g., a transposase, a restriction endonuclease, and/or CRISPR associated protein such as Cas9 or Cas12a) to generate DNA fragments from genomic DNA of a cell. In some embodiments, the method 400 can include: generating a plurality of nucleic acid fragments from double-stranded deoxyribonucleic acid (dsDNA), e.g., gDNA, of a cell. For example, the plurality of nucleic acid fragments may not be generated from amplification. As another example, the plurality of nucleic acid fragments can be, or include, RNA molecules produced by in vitro transcription.

In some embodiments, each of the plurality of nucleic acid fragments can comprise a capture sequence 434a, 434b, a complement of the capture sequence, a reverse complement of the capture sequence, or a combination thereof. The method 400 can include barcoding 424 the plurality of nucleic acid fragments using the plurality of barcodes 444 to generate a plurality of barcoded single-stranded deoxyribonucleic acid (ssDNA) fragments 446 (or a complementary sequence thereof, such as a complement or a reverse complement 446). At least some (e.g., at least 1, 2, 3, 4, 5, 6, 7, 8, 9, 10, 100, 1000, 10000, 100000, 1000000, 10000000, or more) of the plurality of barcodes 444 can comprise a cell label 450, a molecular label 448, and the capture sequence 434 (or a complement of the capture sequence, a reverse complement of the capture sequence, or a combination thereof). Molecular labels 448 of at least two barcodes of the plurality of barcodes 444 comprise different molecular label sequences. At least two barcodes of the plurality of barcodes 444 can comprise cell labels 450 with an identical cell label sequence. The method 400 can include obtaining sequencing data of the plurality of barcoded ssDNA fragments 446 (or a complementary sequence thereof); and determining information relating to the dsDNA (e.g., gDNA) based on the sequences of the plurality ssDNA fragments 445 in the sequencing data obtained.

In some embodiments, the dsDNA (e.g., gDNA) is inside a nucleus 452. The method 400 can optionally include permeabilizing (e.g., at block 402) a nucleus 452 to generate a permeabilized nucleus. The method 400 can optionally include fixating a cell (e.g., at block 402) comprising the nucleus 452 prior to permeabilizing the nucleus.

In some embodiments, the method 400 comprises denaturing 414 the plurality of nucleic acid fragments 440 to generate a plurality of ssDNA fragments 442. Barcoding 424 the plurality of nucleic acid fragments can comprise barcoding 424 the plurality of ssDNA fragments 442 using the plurality of barcodes 444 to generate the plurality of barcoded ssDNA fragments 446 and/or or complementary sequences thereof.

In some embodiments, for any method of sample analysis as described herein, the method further comprises contacting a cell with a nucleic acid reagent as described herein. The nucleic acid reagent can comprise a capture sequence, a barcode, a primer binding site, and a double-stranded DNA-binding agent. The cell can be a dead cell. The nucleic acid reagent can bind to double-stranded DNA in the dead cell. The method can further comprise washing the cell to remove excess of the nucleic acid reagent. The method can further comprise lysing the cell, thereby releasing the nucleic acid reagent. The method can further comprise barcoding the nucleic acid reagent. It is contemplated that dead cells are permeable to the nucleic acid reagent, while live cells are not, or are permeable to no more than trace amounts of the nucleic acid reagent. Accordingly, it is contemplated that the method described herein can identify dead and live cells by identifying whether the nucleic acid reagent has bound to DNA of the cell (for example, by determining whether a barcode associated with the nucleic acid reagent is associated with the cell) and/or determining whether at least a threshold number of nucleic acid reagents has bound to the cell (for example, by determining whether at least a threshold count of barcodes is associated with the nucleic acid reagent is associated with the cell, for example, at least 10, 50, 100, 500, 1000, 5000, or 10000 different barcodes).

Using a Transposome to Generate DNA Fragments

In methods and kits of some embodiments, DNA fragments can be generated with a transposome. As used herein, a "transposome" comprises (i) a double-strand nuclease configured to induce a double-stranded DNA break at a structure comprising dsDNA and (ii) at least two copies of an adapter comprising a capture sequence. The adapter can be configured for addition to an ends of a dsDNA. Thus, the adapter can be configured for adding the capture sequence to ends of dsDNA after the moiety has induced the double-stranded break in the dsDNA. The double-strand nuclease can comprise an enzyme such as a transposase (e.g., Tn5, Tn7, Tn10, Tc3, or a mariner transposase such as Mos1), a restriction endonuclease (e.g., EcoRI, NotI, HindIII, HhaI, BamH1, or Sal I), a CRISPR associated protein (e.g., Cas9 or Cas12a), duplex-specific nuclease (DSN), or a combination of these. It is contemplated that while some double-strand nucleases such as transposase can facilitate the addition of an adaptor to an end of a dsDNA fragment, other, for example restriction endonucleases, do not. As such, a transposome can optionally comprise a ligase (e.g., T4, T7, or Taq DNA ligase). It is further contemplated that a transposome can be targeted to a particular structure comprising dsDNA, for example chromatin, methylated dsDNA, a transcriptional initiation complex, or the like. Accordingly, by targeting the adapters to the structure comprising dsDNA, fragmenting the dsDNA, and barcoding the dsDNA so as to obtain sequence information on the dsDNA, the transposome can provide information about DNA sequences associated with the structure comprises the dsDNA. As such, the transposome can further comprises a moiety that targets the transposome to the structure comprising the dsDNA, for example an antibody (e.g., antibody HTA28 that binds specifically to histone phosphorylated S28 of histone H3, or) or fragment thereof, an aptamer (nucleic acid or peptide), or a DNA binding domain (e.g., a zinc finger binding domain). In any method of sample analysis as described herein, the transposome can target a specified structure comprising dsDNA, for example chromatin, a particular DNA methylation state, a DNA in a specified organelle, or the like. It is contemplated that the method of sample analysis can identify particular DNA sequences associated with structures targeted by the transposome, for example, chromatin-accessible DNA, construct DNA, organelle DNA, or the like. In some embodiments, a kit for sample analysis is described. The kit can comprise a transposome as described herein, and a plurality of barcodes as described herein. The barcodes can be immobilized on particles as described herein.

By way of example, generating the plurality of nucleic acid fragments can comprise: contacting the dsDNA (e.g., gDNA) with a transposome 428, wherein the transposome 428 comprises a double-strand nuclease configured to induce a double-stranded DNA break at a structure comprising dsDNA (e.g., a transposase) 430 and two copies 434a, 434b of an adaptor comprising the capture sequence (e.g., a poly(dT) sequence), to generate a plurality of double-stranded DNA (dsDNA) fragments 440 each comprising a sequence complementary 434a', 434b' to the capture sequence 434a, 434b. For example, the adaptor may not include a 5' overhang, such as a poly(dT) overhang 434a, 434b. The double-strand nuclease (e.g., transposase) 430 can be loaded with the two copies 434a, 434b of the adaptor. In some embodiments, the capture sequence 434a, 434b comprises a poly(dT) region. The sequence complementary 434a' 434b' to the capture sequence can comprise a poly(dA) region.

Generating the plurality of nucleic acid fragments can comprise: contacting 410 the dsDNA (e.g., gDNA) with a transposome 428, wherein the transposome 428 comprises a double-strand nuclease configured to induce a double-stranded DNA break at a structure comprising dsDNA (e.g., transposase) 430 and two copies 432a, 432b of an adaptor having a 5' overhang 434a, 434b comprising a capture sequence, to generate a plurality of double-stranded DNA (dsDNA) fragments 438 each with two copies of the 5' overhangs 434a, 434b. The double-strand nuclease 430 can be loaded with the two copies 432a, 432b of the adaptor. The method 400 can, in some embodiments, include contacting 412 the plurality dsDNA fragments 438 having the 5' overhangs 434a, 434b with a polymerase to generate the plurality of nucleic acid fragments 440 comprising a plurality of dsDNA fragments each comprising a complementary sequence 434a', 434b' (e.g., a complement, or a reverse complement) to at least a portion of the 5' overhang. In some embodiments, none of the plurality of dsDNA fragments 442 comprises an overhang (e.g., a 3' overhang or a 5' overhang like the 5' overhangs 434a', 434b').

Higher Signal Intensity

For capturing genomic and chromatin accessibility information, the signal (e.g., the number of dsDNA fragments of interest, such as the dsDNA fragments for chromatin accessibility analysis, can be further amplified by incorporating a promoter (e.g., a T7 promoter) in front of the poly(dA) tail in the transposome 428. For example, dsDNA (e.g., gDNA) can be amplified further (e.g., 1000-fold) by incorporating in vitro transcription within the nuclei 452 or cell prior to loading onto a single cell system or platform 416. For example, a T7 promoter 502 in the sequence can be appended to the ends of dsDNA (e.g., gDNA) fragments.

After transposition and adding of the poly(dT) sequence and the promoter, incubate fixed cells or nuclei with in vitro transcription (IVT) reaction mix. Thousands of copies of the RNA carrying the dsDNA (e.g., gDNA) sequence would be produced and contained within the fixed cell or nuclei. The single cell capture and lysis (e.g., at block 418 in FIGS. 4A-4B) method can occur as described herein.

Figure 5A:
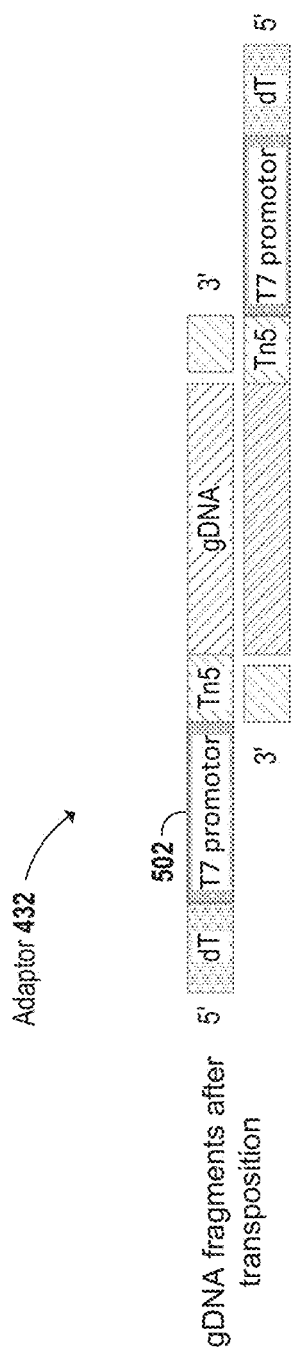
FIGS. 5A-5B schematically illustrate a non-limiting exemplary method of capturing of genomic and chromatic accessibility information from single cells with improved signal intensity.
Figure 5B:
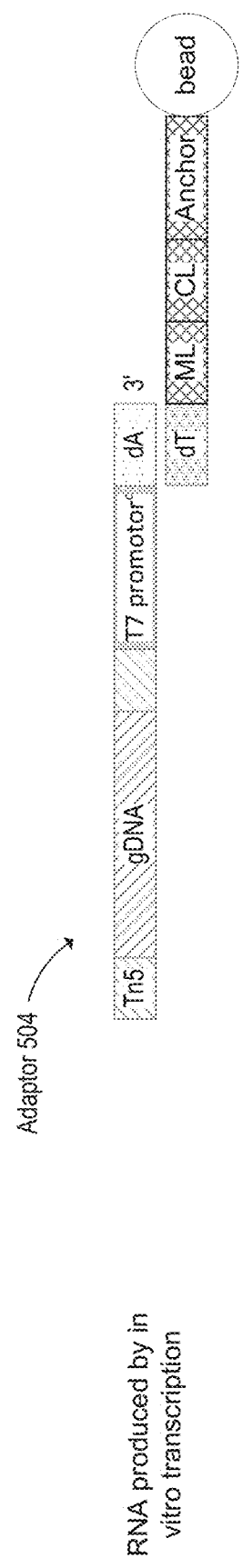

FIGS. 5A-5B schematically illustrate a non-limiting exemplary method of capturing of genomic and chromatic accessibility information from single cells with improved signal intensity. In some embodiments, the adaptor 432*a*, 432*b* optionally comprises a promoter sequence. The promoter sequence can comprise a T7 promoter sequence 502. Generating the plurality of nucleic acid fragments can comprise transcribing the plurality of dsDNA fragments using in vitro transcription to generate a plurality of ribonucleic acid (RNA) molecules 504. Barcoding 424 the plurality of nucleic acid fragments comprises barcoding the plurality of RNA molecules 504.

Using a Restriction Enzyme to Generate dsDNA Fragments with Blunt Ends

In some embodiments, generating the plurality of nucleic acid fragments comprises: fragmenting the dsDNA (e.g., gDNA) to generate a plurality of dsDNA fragments with blunt ends using a restriction enzyme. Fragmenting the dsDNA (e.g., gDNA) can comprise contacting the dsDNA (e.g., gDNA) with a restriction enzyme to generate the plurality of dsDNA fragments each with blunt ends. At least one of the plurality of dsDNA fragments can comprise a blunt end. At least one of the plurality of dsDNA fragments can comprise a 5' overhang or a 3' overhang. None of the plurality of dsDNA fragments can comprise a blunt end. Fragmenting the dsDNA (e.g., gDNA) can comprise contacting the double-stranded gDNA with a restriction enzyme to generate the plurality of dsDNA fragments with blunt ends. At least one, some, or all of the dsDNA fragments can include blunt ends.

Using CRISPR Associated Protein to Generate dsDNA Fragments

In some embodiments, generating the plurality of nucleic acid fragments comprises: fragmenting the dsDNA (e.g., gDNA) to generate a plurality of double stranded deoxyribonucleic acid (dsDNA) fragments using a CRISPR associated protein such as Cas9 of Cas12a. Fragmenting the dsDNA (e.g., gDNA) can comprise contacting the double-stranded gDNA with the CRISPR associated protein to generate the plurality of dsDNA fragments. At least one, some, or all of the dsDNA fragments can include blunt ends. It is contemplated that in some embodiments, breaks in the dsDNA can be targeted to particular sequences or motifs using a guide RNA (gRNA) targeting the particular sequence or motif, so that the CRISPR associated protein induces double-stranded breaks at the particular sequence or motif.

Generating Nucleic Acid Fragments

In some embodiments, generating the plurality of nucleic acid fragments (e.g., using a restriction enzyme or CRISPR associated protein) comprises: appending (e.g., at block 410 discussed with reference to FIGS. 4A-4B) two copies of an adaptor comprising a sequence complementary to a capture sequence to at least some (e.g., at least 1, 2, 3, 4, 5, 6, 7, 8, 9, 10, 100, 1000, 10000, 100000, 1000000, 10000000, or more) of the plurality of dsDNA fragments to generate a plurality of dsDNA fragments (e.g., a plurality of dsDNA fragments with blunt ends). Appending the two copies of the adaptor can comprise ligating the two copies of the adaptor to at least some (e.g., at least 1, 2, 3, 4, 5, 6, 7, 8, 9, 10, 100, 1000, 10000, 100000, 1000000, 10000000, or more) of the plurality of dsDNA fragments to generate the plurality of dsDNA fragments comprising the adaptor.

Using a Restriction Enzyme to Generate dsDNA Fragments with Overhangs

In some embodiments, generating the plurality of nucleic acid fragments comprises: fragmenting the dsDNA (e.g., gDNA) to generate a plurality of dsDNA fragments with overhangs using a restriction enzyme so adaptors do not need to be added. Fragmenting the dsDNA (e.g., gDNA) can comprise contacting the dsDNA (e.g., gDNA) with a restriction enzyme to generate the plurality of dsDNA fragments, wherein at least one of the plurality of dsDNA fragments comprises the capture sequence. The capture sequence can be complementary to the sequences of the 5' overhangs. The sequence complementary to the capture sequence can comprise the sequence of the 5' overhang.

Chromatin Accessibility

Referring to FIGS. 4A-4B, for capturing chromatin accessibility information 406*a*, nuclei 452 can be incubated with enzymatic cutters (e.g., a transposase, a restriction enzyme, and Cas9) and dsDNA (e.g., gDNA) fragments can be appended with adaptors 432*a*, 432*b*. The cutting can occur at locations where the chromatins are exposed (e.g., most exposed, more exposed than average, and exposed to a desirable extent). For example, a transposase 432 can insert the adaptors 432*a*, 432*b* into the dsDNA (e.g., gDNA).

In some embodiments, determining the information relating to the dsDNA (e.g., gDNA) comprises determining chromatin accessibility 406*a* of the dsDNA (e.g., gDNA) based on the sequences and/or abundance of the plurality ssDNA fragments 442 in the sequencing data obtained. Determining the chromatin accessibility 442 of the dsDNA (e.g., gDNA) can comprise: aligning the sequences of the plurality of ssDNA fragments 442 to a reference sequence of the dsDNA (e.g., gDNA); determining regions of the dsDNA (e.g., gDNA) corresponding the ends of ssDNA fragments of the plurality of ssDNA fragments 442 to be accessible or have certain accessibility (e.g., highly accessible, above average accessibility, and accessibility above a threshold or desired extent). Determining the chromatin accessibility of the dsDNA (e.g., gDNA) can comprise: aligning the sequences of the plurality of ssDNA fragments to a reference sequence of the dsDNA (e.g., gDNA); and determining the accessibility of regions of the dsDNA (e.g., gDNA) corresponding the ends of ssDNA fragments of the plurality of ssDNA fragments based on the numbers of the ssDNA fragments of the plurality of ssDNA fragments in the sequencing data.

For example, the cutting can occur at locations where the chromatins have above average accessibility. Regions of the dsDNA (e.g., gDNA) that correspond to the ends of ssDNA fragments can have above average accessibility. Such regions of the dsDNA (e.g., gDNA) can have above average abundance in the sequencing data obtained. As another example, the dsDNA (e.g., gDNA) comprises region A-region B1-region B2-region C. If region B1 and region B2 have above average accessibility while region A and region C have below average accessibility, region B1 and region B2 can be cut (e.g., between region B1 and region B2), while region A and region C are not cut. The sequencing data can include above average abundance of sequences of region B1 and region B2 where the cut occurs (and around where the cut occurs). Sequences of region A and region C may not be present (or have low abundance) in the sequencing data. Thus, the chromatic accessibility of the dsDNA (e.g., gDNA) can be determined based on the sequence and the number of each of the plurality of ssDNA fragments.

Genome Information

For capturing genome information 406b, nuclei 452 can be first exposed to reagents to digest 408 the nucleosome structure (e.g., to remove nucleosome/histone proteins), before subjecting to enzymatic cutters and addition of adaptors. In some embodiments, determining the information relating to the dsDNA (e.g., gDNA) comprises determining genome information 406b of the dsDNA (e.g., gDNA) based on the sequences of the plurality ssDNA fragments 442 in the sequencing data obtained. The method can comprise digesting 408 nucleosomes associated with the double-stranded dsDNA (e.g., gDNA). Determining the genome information of the dsDNA (e.g., gDNA) can comprise: determining at least a partial sequence of the dsDNA (e.g., gDNA) by aligning the sequences of the plurality of ssDNA fragments 442 to a reference sequence of the dsDNA (e.g., gDNA). In some embodiments, a full or partial genome of a cell can be determined. In some embodiments, the dsDNA is genomic DNA (gDNA) of a cell. In some embodiments, the dsDNA is genomic DNA of an organelle of the cell, for example a mitochondrion or chloroplast.

Methylome Information

For capturing methylome information 406c, after dsDNA (e.g., gDNA) fragments are captured by the capture probe 444 and remain single stranded 442, bisulfate treatment 422 is used to turn methyl cytosine bases 454mc into thymine bases. Subsequently, the dsDNA (e.g., gDNA) can be copied by RT 424 or DNA polymerase.

In some embodiments, determining the information relating to the dsDNA (e.g., gDNA) comprises determining methylome information 406c of the dsDNA (e.g., gDNA) based on the sequences of the plurality ssDNA fragments 442 in the sequencing data obtained. The method can comprise: digesting 408 nucleosomes associated with the dsDNA (e.g., gDNA). The method 400 can comprise: performing bisulfite conversion 422 of cytosine bases of the plurality of single-stranded DNA 442 to generate a plurality of bisulfite-converted ssDNA 442b with uracil bases 454u. Barcoding 424 the plurality of ssDNA fragments 442 can comprise barcoding 424 the plurality of bisulfite-converted ssDNA 452b using the plurality of barcodes 444 to generate the plurality of barcoded ssDNA fragments 446 and/or or complementary sequences thereof. Determining the methylome information 406c can comprise: determining a position of the plurality ssDNA fragments 442 in the sequencing data has a thymine base (or uracil base 454u) and the corresponding position in a reference sequence of the dsDNA (e.g., gDNA) has a cytosine base to determine the corresponding position in the dsDNA (e.g., gDNA) has a methylcytosine base 454mc.

In some embodiments, determining the methylome information comprises a method of sample analysis comprising contacting double-stranded deoxyribonucleic acid (dsDNA) from a cell with a transposome, in which the transposome comprises a double-strand nuclease configured to induce a double-stranded DNA break at a structure comprising dsDNA loaded with two copies of an adaptor having a 5' overhang comprising a capture sequence to generate a plurality of overhang dsDNA fragments each comprising two copies of the 5' overhangs. The method can further comprise contacting the plurality of overhang dsDNA fragments with a polymerase to generate a plurality of complementary dsDNA fragments each comprising a complementary sequence to at least a portion of each of the 5' overhang, denaturing the plurality of complementary dsDNA fragments to generate a plurality of single-stranded DNA (ssDNA) fragments, barcoding the plurality of ssDNA fragments using a plurality of barcodes to generate a plurality of barcoded ssDNA fragments, in which each of the plurality of barcodes comprises a cell label sequence, a molecular label sequence, and the capture sequence, wherein which at least two of the plurality of barcodes comprise different molecular label sequences, and in which at least two of the plurality of barcodes comprise an identical cell label sequence, obtaining sequencing data of the plurality of barcoded ssDNA fragments, and determining information relating to the dsDNA based on sequences of the plurality of barcoded ssDNA fragments in the sequencing data. In some embodiments, the method further comprises capturing a ssDNA fragment of the plurality of barcoded ssDNA fragments on a particle comprising an oligonucleotide comprising the capture sequence, the cell label sequence and the molecular label sequence. By way of example, the capture sequence can comprise a poly dT sequence that binds to a poly A tail on the ssDNA fragment. The captured ssDNA fragment can comprise a methylated cytidine, performing a bisulfide conversion reaction on the ssDNA fragment to convert the methylated cytidine to a thymidine, extending the ssDNA fragment in the 5' to 3' direction to produce the barcoded ssDNA fragment comprising the thymidine, the barcoded ssDNA comprising the capture sequence, molecular label sequence, and cell label sequence, extending the oligonucleotide in the 5' to 3' direction using a reverse transcriptase or polymerase or combination thereof to produce a complementary DNA strand complementary to the barcoded ssDNA comprising the thymidine, denaturing the barcoded ssDNA and complementary DNA strand to produce single stranded sequences, and amplifying the single stranded sequences.

In some embodiments, obtaining the methylome information comprises determining a position of the plurality ssDNA fragments in the sequencing data has a thymine base and the corresponding position in a reference sequence of the dsDNA has a cytosine base comprising a bisulfide conversion of a methylated cytosine of a ssDNA fragment of the plurality, thus converting the methylated cytosine base to the thymine base, and determining the corresponding position of the thymine base in the reference sequence to be a cytosine base.

Multiomics

In some embodiments, the method can include: barcoding a plurality of targets (e.g., targets in the nucleus 452) using the plurality of barcodes 444 to generate a plurality of barcoded targets; and obtaining sequencing data of the barcoded targets. The targets can be nucleic acid targets, such as mRNA targets, sample indexing oligonucleotides (e.g., described in U.S. application Ser. No. 15/937,713, published as US 2018/0346970, which is incorporated by reference in its entirety herein), and oligonucleotides for determining protein expression (e.g., described in U.S. application Ser. No. 15/715,028, published as US 2018/0088112, which is incorporated by reference in its entirety herein). In some embodiments, two or more of the genome, chromatin accessibility, methylome, transcriptome, and proteome information can be determined in single cells.

In some embodiments, a method of sample analysis comprises contacting double-stranded deoxyribonucleic acid (dsDNA) from a cell with a transposome, wherein the transposome comprises a double-strand nuclease configured to induce a double-stranded DNA break at a structure comprising dsDNA loaded with two copies of an adaptor having a 5' overhang comprising a capture sequence to generate a plurality of overhang dsDNA fragments each comprising two copies of the 5' overhangs, contacting the plurality of overhang dsDNA fragments with a polymerase to generate a plurality of complementary dsDNA fragments each comprising a complementary sequence to at least a portion of each of the 5' overhang, denaturing the plurality of complementary dsDNA fragments to generate a plurality of single-stranded DNA (ssDNA) fragments, barcoding the plurality of ssDNA fragments using a plurality of barcodes to generate a plurality of barcoded ssDNA fragments, wherein each of the plurality of barcodes comprises a cell label sequence, a molecular label sequence, and the capture sequence, wherein at least two of the plurality of barcodes comprise different molecular label sequences, and wherein at least two of the plurality of barcodes comprise an identical cell label sequence, obtaining sequencing data of the plurality of barcoded ssDNA fragments, and determining information relating to the dsDNA based on sequences of the plurality of barcoded ssDNA fragments in the sequencing data. In some embodiments, the method further comprises contacting a cell with a nucleic acid reagent, the nucleic acid reagent comprising a capture sequence, a barcode, a primer binding site, and a double-stranded DNA-binding agent, wherein the cell is a dead cell, and wherein the nucleic binding reagent binds to double-stranded DNA in the dead cell, washing the dead cell to remove excess of the nucleic acid reagent, lysing the dead cell, thereby releasing the nucleic acid reagent, and barcoding the nucleic acid reagent.

In some embodiments of the method of sample analysis, the cell is associated with a solid support comprising an oligonucleotide comprising a cell label sequence, and wherein barcoding comprises barcoding the nucleic acid reagent with the cell label sequence.

In some embodiments of the method of sample analysis, the solid support comprises a plurality of the oligonucleotides, each comprising the cell label sequence and a different molecular label sequence.

In some embodiments, the method of sample analysis further comprises sequencing the barcoded nucleic acid reagents, and determining a presence of a dead cell based on the presence of the barcode of the nucleic acid reagent.

In some embodiments, the method of sample analysis further comprises associating two or more cells each with different solid supports comprising different cell labels, whereby each of the two or more cells is associated one-to-one with a different cell label.

In some embodiments, the method of sample analysis further comprises determining a number of dead cells in the sample based on the number of unique the cell labels associated with a barcode of a nucleic acid reagent.

In some embodiments, the method of sample analysis comprises determining the number of molecular label sequences with distinct sequences associated with the cell label and the control barcode sequence comprises determining the number of molecular label sequences with the highest number of distinct sequences associated with the cell label and the control barcode sequence for each cell label in the sequencing data.

In some embodiments of the method of sample analysis, the cell is a live cell, and wherein the nucleic acid reagent does not enter the live cell, and thus does not bind to double-stranded DNA in the live cell.

In some embodiments, the method of sample analysis further comprises contacting a dead cell with a protein binding reagent associated with a unique identifier oligonucleotide, whereby the protein binding reagent binds to a protein of the dead cell, and barcoding the unique identifier oligonucleotide.

In some embodiments of the method of sample analysis, the protein binding reagent comprises an antibody, a tetramer, an aptamer, a protein scaffold, an invasin, or a combination thereof. In some embodiments, the protein binding reagent comprises an antibody or fragments thereof, aptamer, small molecule, ligand, peptide, oligonucleotide, or any combination thereof. By way of example, the protein binding reagent can comprise, consist essentially of, or consist of a polyclonal antibody, monoclonal antibody, recombinant antibody, single-chain antibody (scAb), or a fragments thereof, such as Fab, Fv, scFv, or the like. By way of example, the antibody can comprise, consist essentially of, or consist of an Abseq antibody (See Shahi et al. (2017), Sci Rep. 7:44447, the content of which is hereby incorporated by reference in its entirety). The unique identifier of the protein binding reagent can comprise a nucleotide sequence. In some embodiments, the unique identifier comprises a nucleotide sequence of 25-45 nucleotides in length. In some embodiments, the unique identifier is not homologous to genomic sequences of the sample or cell. In some embodiments, the protein binding reagent can be associated with the unique identifier oligonucleotide covalently. In some embodiments, the protein binding reagent can be associated with the unique identifier oligonucleotide covalently. For example, the protein binding reagent can be associated with the unique identifier oligonucleotide through a linker. In some embodiments, the linker can comprise a chemical group that reversibly attaches the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, streptavidin, biotin, amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. In some embodiments, each protein binding reagent can be conjugated with a single oligonucleotide molecule. In some embodiments, each protein binding reagent can be conjugated with more than one oligonucleotide molecule, for example, at least 2, at least 3, at least 4, at least 5, at least 10, at least 20, at least 30, at least 40, at least 50, at least 100, at least 1,000, or more oligonucleotide molecules, wherein each of the oligonucleotide molecule comprises the same unique identifier.

In some embodiments of the method of sample analysis, a protein target of the protein binding reagent is selected from a group comprising 10-100 different protein targets, or a cellular component target of the cellular component binding reagent is selected from a group comprising 10-100 different cellular component targets.

In some embodiments of the method of sample analysis, a protein target of the protein binding reagent comprises a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof.

In some embodiments of the method of sample analysis, the protein binding reagent comprises an antibody or fragment thereof that binds to a cell surface protein.

In some embodiments of the method of sample analysis, the barcoding is with a barcode comprising a molecular label sequence.

In some embodiments, a method of sample analysis comprises contacting a dead cell of a sample with a nucleic acid reagent. The nucleic acid reagent can comprise, consist essentially of, or consists of any nucleic acid agent as described herein. For example, the nucleic acid binding agent can comprise a capture sequence, a barcode, a primer binding site, and a double-stranded DNA-binding agent. By way of example, the barcode can comprise a cell label, a molecular label, and a target-binding region as described herein. The nucleic acid reagent can bind to double-stranded DNA in the dead cell. The method can comprise washing excess nucleic acid reagent from the dead cell, for example, by centrifuging the sample, aspirating fluid from the sample, and applying a new fluid such as a buffer to the sample. The washing can remove unbound nucleic acid reagent, while double-stranded-DNA-bound nucleic binding reagent can remain bound to the double-stranded DNA of the dead cell. It is contemplated that for live cells, the washing will remove all (or remove all but trace amounts of the nucleic acid reagent). The method can comprise lysing the dead cell. The lysing can release the nucleic acid reagent from the dead cell. By way of example, the dead cell can be lysed with lysed by addition of a cell lysis buffer comprising a detergent (e.g., SDS, Li dodecyl sulfate, Triton X-100, Tween-20, or NP-40), an organic solvent (e.g., methanol or acetone), a digestive enzyme (e.g., proteinase K, pepsin, or trypsin), or any combination thereof. The method can comprise barcoding the nucleic acid reagent as described herein. The barcoding can produce a nucleic acid of comprising the barcode of the nucleic acid reagent (or a complement thereof) labeled with a cell label. Optionally, the nucleic acid can further comprise a molecular label. It is contemplated that the cell label can associate the nucleic acid reagent one-to-one with a cell (e.g., the dead cell), and the molecular label can be used to quantify the number of nucleic acid reagents associated with a single cell (e.g., the dead cell).

In some embodiments of a method of sample analysis, barcoding comprises capturing the dead cell on a solid support, such as a bead, the solid support comprising a cell label sequence and a molecular label sequence.

In some embodiments, a method of sample analysis further comprises determining a number of distinct molecular label sequences associated with each cell label sequence, and determining a number of dead cells in the sample based on the number of distinct cell label sequences associated with molecular label sequences. For example, in some embodiments, a presence of a barcode of a nucleic acid reagent as described herein can indicate that a cell is a dead cell. For example, in some embodiments, a quantity of barcodes of nucleic acid reagents that exceed a threshold can indicate that a cell is a dead cell. The threshold can comprise, for example, a limit of detection, or a quantity of barcodes of nucleic acid reagents that exceeds a negative control, for example a known live cell. In some embodiments, a quantity of at least 10, 50, 100, 500, 1000, 5000, or 10000 barcodes of nucleic acid reagents associated with the cell can indicate that the cell is a dead cell.

In some embodiments of a method of sample analysis, determining the number of molecular label sequences with distinct sequences associated with the cell label and the control barcode sequence comprises determining the number of molecular label sequences with the highest number of distinct sequences associated with the cell label for each cell label in the sequencing data.

In some embodiments, a method of sample analysis further comprises contacting a dead cell with a protein binding reagent associated with a unique identifier oligonucleotide, whereby the protein binding reagent binds to a protein of the dead cell. The method can further comprise barcoding the unique identifier oligonucleotide. Optionally the protein binding reagent can be contacted with the dead cell before washing the dead cell. In some embodiments, the dead cell is contacted with two or more different protein binding reagents, each associated with a unique identifier oligonucleotide. Thus, at least two different proteins of the dead cell, if present, can be bound with the different protein binding reagents.

In some embodiments of a method of sample analysis, the protein binding reagent is associated with two or more sample indexing oligonucleotides with an identical sequence.

In some embodiments of a method of sample analysis, the protein binding reagent is associated with two or more sample indexing oligonucleotides with different sample indexing sequences.

In some embodiments of a method of sample analysis, the protein binding reagent comprises an antibody, a tetramer, an aptamer, a protein scaffold, an invasin, or a combination thereof.

In some embodiments of a method of sample analysis, a protein target of the protein binding reagent is selected from a group comprising 10-100 different protein targets, or wherein a cellular component target of the cellular component binding reagent is selected from a group comprising 10-100 different cellular component targets.

In some embodiments of a method of sample analysis, a protein target of the protein binding reagent comprises a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof.

In some embodiments of a method of sample analysis, the protein binding reagent comprises an antibody or fragment thereof that binds to a cell surface protein.

In some embodiments of a method of sample analysis, the capture sequence and the sequence complementary to the capture sequence are a specified pair of complementary nucleic acids of at least 5 nucleotides to about 25 nucleotides in length.

In some embodiments, a method of sample analysis comprises contacting double-stranded deoxyribonucleic acid (dsDNA) from a cell with a transposome. The transposome can comprise a double-strand nuclease configured to induce a double-stranded DNA break at a structure comprising dsDNA loaded with two copies of an adaptor having a 5' overhang comprising a capture sequence to generate a plurality of overhang dsDNA fragments each comprising two copies of the 5' overhangs. The method can comprise contacting the plurality of overhang dsDNA fragments with a polymerase to generate a plurality of complementary dsDNA fragments each comprising a complementary sequence to at least a portion of each of the 5' overhang. The method can comprise denaturing the plurality of complementary dsDNA fragments to generate a plurality of single-stranded DNA (ssDNA) fragments. The method can comprise barcoding the plurality of ssDNA fragments using a plurality of barcodes to generate a plurality of barcoded ssDNA fragments, in which each of the plurality of barcodes comprises a cell label sequence, a molecular label sequence, and the capture sequence. All of the cell label sequences associated with a single cell can be the same, so as to associate each single cell, one-to-one, with a cell label sequence. At least two of the plurality of barcodes can comprise different molecular label sequences. The method can comprise obtaining sequencing data of the plurality of barcoded ssDNA fragments. The method can comprise quantifying a quantity of the dsDNA in the cell based on a quantity of unique molecular label sequences associated with the same cell label sequence.

In some embodiments, a method of sample analysis further comprises capturing a ssDNA fragment of the plurality of ssDNA fragments on a solid support comprising an oligonucleotide comprising the capture sequence, the cell label sequence, and the molecular label sequence. The capture sequence can comprise a target-binding sequence that hybridizes to a sequence of the ssDNA fragment that is complementary to the target-binding sequence. For example, the capture sequence can comprise a poly dT sequence that binds to a poly A tail on the ssDNA fragment. The method can comprise extending the ssDNA fragment in the 5' to 3' direction to produce the barcoded ssDNA fragment. For example, the extending can be performed with a DNA polymerase. The barcoded ssDNA can comprise the capture sequence, molecular label sequence, and cell label sequence. The method can comprise extending the oligonucleotide in the 5' to 3' direction using a reverse transcriptase or polymerase or combination thereof to produce a complementary DNA strand complementary to the barcoded ssDNA. The method can comprise denaturing the barcoded ssDNA and complementary DNA strand to produce single stranded sequences. The method can comprise amplifying the single stranded sequences.

In some embodiments, the method of sample analysis further comprises bisulfate conversion of cytosine bases of the plurality of ssDNA fragments to generate a plurality of bisulfate-converted ssDNA fragments comprising uracil bases. Accordingly, it is contemplated that when complementary DNA strands complementary to the barcoded ssDNAs are produced, the positions complementary to the uracil bases will comprise adenine (rather than guanine, as would be expected if the cytosine base had not been methylated and thus remained a cytosine after the bisulfite conversion process). Accordingly, it is contemplated that the presence of adenine (rather than guanine) at positions expected to comprise guanine on the complementary DNA strands can indicate methylation of a cytosine at that position. The presence of the adenine can be determined by directly sequencing the complementary DNA strand, or by sequencing its complement. Optionally, the sequence can be compared to a reference sequence, such as a genomic reference sequence. The reference sequence can be an electronically stored reference.

Barcoding

In some embodiments, the barcoding 424 comprises loading cells 416 onto a single cell platform. ssDNA fragments 442 or nucleic acids can hybridize 420 to the capture sequence 434 for barcoding. Barcoded ssDNA fragments 446, a complement, a reverse complement 446rc, or a combination thereof, can be amplified 426 prior to and/or for sequencing as described with reference to FIG. 3.

In some embodiments, the barcoding 424 can include: stochastically barcoding the plurality of ssDNA fragments 442 or the plurality of nucleic acids using the plurality of barcodes 444 to generate a plurality of stochastically barcoded ssDNA fragments 446. The barcoding 424 can comprise: barcoding the plurality of ssDNA fragments 442 using the plurality of barcodes 444 associated with a particle 456 to generate the plurality of barcoded ssDNA fragments 446, wherein the barcodes 444 associated with the particle 456 comprise an identical cell label sequence and at least 100 different molecular label sequences.

In some embodiments, at least one barcode the plurality of barcodes can be immobilized on the particle. At least one barcode of the plurality of barcodes can partially immobilized on the particle. At least one barcode of the plurality of barcodes can be enclosed in the particle. At least one barcode of the plurality of barcodes can be partially enclosed in the particle. The particle can be disruptable (e.g., dissolvable, or degradable). The particle can comprise a disruptable hydrogel particle. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof.

In some embodiments, the barcodes of the particle can comprise molecular labels with at least 1000 different molecular label sequences. The barcodes of the particle can comprise molecular labels with at least 10000 different molecular label sequences. The molecular labels of the barcodes can comprise random sequences. The particle can comprise at least 10000 barcodes.

Barcoding the plurality of ssDNA fragments can comprise: contacting the plurality of ssDNA fragments with the capture sequence of the plurality of barcodes; and transcribing the plurality ssDNA using the plurality of barcodes to generate the plurality of barcoded ssDNA fragments. The method can include: prior to obtaining the sequencing data of the plurality of barcoded ssDNA fragments, amplifying the plurality of barcoded ssDNA fragments to generate a plurality of amplified barcoded DNA fragments. Amplifying the plurality of barcoded ssDNA fragments can comprise: amplifying the barcoded ssDNA fragments by polymerase chain reaction (PCR).

Nucleic Acid Reagents

In some embodiments, a nucleic acid reagent comprises, consists essentially of, or consists of a capture sequence, a barcode, a primer binding site, and a double-stranded DNA-binding agent. The barcode of the nucleic acid reagent can comprise an identifier sequence, indicating that the barcode is associated with the nucleic acid reagent. Optionally, in accordance with the methods and kits as described herein, different molecule nucleic acid reagents can comprise different barcode sequences. The nucleic acid can be used in any of the methods of sample analysis as described herein. In some embodiments, a kit comprises, consists essentially of, or consists of a nucleic acid reagent as described herein. Optionally, the kit further comprises a solid support (e.g., a particle) as described herein. A plurality of barcodes as described herein can be immobilized on the solid support.

Figure 6:
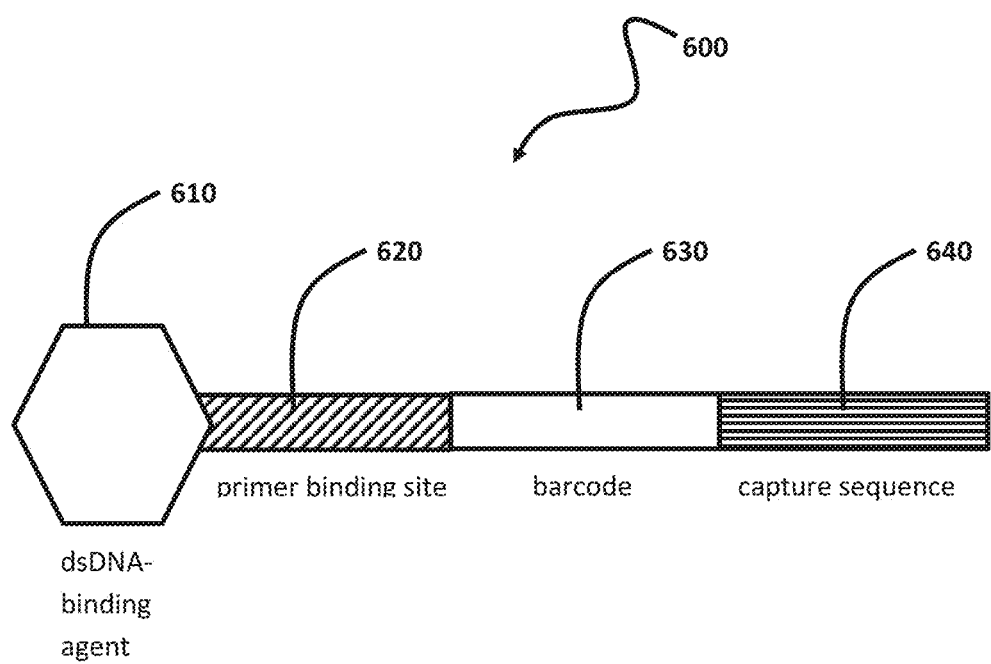
FIG. 6 schematically illustrates a non-limiting exemplary nucleic acid reagent of some embodiments.

An example nucleic acid reagent 600 of some embodiments is illustrated in FIG. 6. The nucleic acid reagent 600 can comprise a double-stranded DNA-binding agent 610. The nucleic acid reagent 600 can comprise a primer binding site 620, for example a PCR handle. The nucleic acid reagent 600 can comprise a barcode 630. The barcode can comprise a unique identifier sequence. The nucleic acid reagent 600 can comprise a capture sequence 640, for example, a poly (A) tail.

In some embodiments, the nucleic acid reagent is plasma-membrane impermeable. Without being limited by theory, it is contemplated that such a nucleic acid reagent cannot pass through an intact plasma membrane (or can pass through an intact plasma membrane in no more than trace amounts), and therefore, will not enter the nuclei of live cells (or will not enter the nuclei of live cells in any more than trace amounts). In contrast, the nucleic acid reagent can enter the nuclei of dead cells because the plasma membrane of dead cells are not intact. In some embodiments, the nucleic acid reagent is configured to specifically bind to dead cells, and nucleic acid reagent does not bind to live cells.

In some embodiments of the nucleic acid reagent, the capture sequence comprises a poly(A) region.

In some embodiments of the nucleic acid reagent, the primer binding site comprises a universal primer binding site.

In some embodiments, a method of binding a nucleic acid reagent to a cell is described. The method can comprise labeling cells of a sample with nucleic acid reagents. Excess nucleic acid reagents can be washed away. Optionally, the cells are also labeled with one or more barcodes as described herein, for example protein binding reagents associated with a unique identifier sequence, for example an Abseq antibody. The cells can then be associated with a particle comprising barcodes immobilized thereon. Nucleic acids of the cell (e.g., mRNA) and/or unique identifier sequences (of protein binding reagents such as Abseq antibodies), and nucleic binding reagents of the cell can be associated with a single cell label, for example immobilized on a solid support, or in a partition. The nucleic acids can be barcoded with the single cell label and a molecular label as described herein. A library of the barcoded nucleic acids can be prepared. The library can be sequenced. It is noted that in addition to providing information on counts of proteins and/or nucleic acids of the cells, the sequencing can provide information on whether the nucleic acid reagent (or a threshold quantity of the nucleic acid reagent) was associated with the cell. The association of the nucleic acid reagent with the cell or threshold quantity of nucleic acid reagent (e.g., at least 10, 50, 100, 500, 1000, 5000, or 10000 molecules of nucleic acid reagent) with the cell can indicate that the cell is a dead cell.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc.

As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method, comprising:
   providing a plurality of transposed nuclei, wherein the plurality of transposed nuclei is generated by contacting a nuclei suspension derived from a sample comprising a plurality of cells with a transposome,
     wherein the transposome comprises a first adaptor, a second adaptor, a double-strand nuclease configured to induce one or more breaks at a structure comprising double-stranded DNA (dsDNA), and a moiety that targets the transposome to the structure comprising dsDNA,
     wherein said contacting generates a plurality of dsDNA fragments each comprising the first adaptor and the second adaptor;
     wherein the first adaptor comprises a first universal sequence,
     wherein the second adaptor comprises a second universal sequence,
     wherein the first universal sequence and the second universal sequence are different from each other and comprise at least a portion of a universal primer, or a complement thereof, and
     wherein the dsDNA fragments comprise one or more single-stranded regions;
   partitioning the plurality of transposed nuclei and a plurality of beads to a plurality of partitions,
     wherein at least one partition of said plurality of partitions comprises a single transposed nuclei from said plurality of transposed nuclei and a single bead from said plurality of beads,
     wherein a plurality of barcodes are associated with each bead, wherein said barcodes each comprise a cell label and a capture probe, wherein the capture probe is 3' of the cell label, wherein barcodes associated with the same bead comprise the same cell label sequence, wherein barcodes associated with different beads comprise different cell label sequences, and wherein the capture probe comprises a sequence configured to bind the first universal sequence, or a complement thereof,
   conducting a linear amplification reaction in one or more of the plurality of partitions, comprising:
     (i) contacting the dsDNA fragments with one or more enzymes configured to fill in the single-stranded regions and generate dsDNA fragments comprising a first DNA strand and a second DNA strand;
     (ii) denaturing the dsDNA fragments;
     (iii) hybridizing barcodes to each second DNA strand via the capture probe;
     (iv) extending said hybridized barcodes to generate barcoded single-stranded deoxyribonucleic acid (ssDNA) fragments;
     (v) denaturing to separate said barcoded ssDNA fragments from the second strands; and
     (vi) repeating steps (iii)-(v) one or more times to generate a plurality of barcoded ssDNA fragments;
   pooling the plurality of barcoded ssDNA fragments of one or more of the plurality of partitions to generate a pool of barcoded ssDNA fragments;
   amplifying the pool of barcoded ssDNA fragments using a first primer capable of hybridizing to the barcode and a second primer capable of hybridizing to the second universal sequence generate a plurality of barcoded amplicons.

2. The method of claim 1, comprising:
   obtaining sequencing data of the plurality of barcoded amplicons, or products thereof; and
   determining chromatin accessibility of the dsDNA based on the sequences of the plurality of barcoded amplicons, or products thereof, in the sequencing data obtained.

3. The method of claim 1,
   wherein the first universal sequence comprises the sequence of at least a portion of an Illumina read 1 sequencing primer, or a complement thereof; and/or
   wherein the second universal sequence comprises the sequence of at least a portion of an Illumina read 2 sequencing primer, or a complement thereof.

4. The method of claim 1, wherein each barcode comprises an Illumina P5 sequence, or a complement thereof, located 5' of the cell label.

5. The method of claim 1, wherein the cell label is 16 nucleotides in length.

6. The method of claim 1, wherein the one or more enzymes comprise a polymerase and/or a ligase.

7. The method of claim 1, wherein none of the plurality of dsDNA fragments comprises an overhang.

8. The method of claim 1, wherein the first adaptor and/or the second adaptor comprise a 5' overhang and/or a 3' overhang, wherein the dsDNA fragments comprise the 5' overhang and/or the 3' overhang, and wherein the one or more enzymes fill in the 5' overhang and/or the 3' overhang.

9. The method of claim 1, wherein the second primer comprises a sample index, an Illumina P7 sequence, complements thereof, or any combination thereof.

10. The method of claim 1, wherein the first adaptor and/or the second adaptor comprises a DNA end sequence of a transposon.

11. The method of claim 1, wherein the double-strand nuclease comprises a transposase.

12. The method of claim 11, wherein the transposase is selected from the group comprising Tn5, Tn7, Tn10, Tc3, a mariner transposase, or any combination thereof.

13. The method of claim 1, wherein the dsDNA is inside the nuclei during the contacting of the dsDNA of the nuclei suspension with the transposome.

14. The method of claim 1, wherein the plurality of partitions comprise fluid droplets.

15. The method of claim 1, comprising permeabilizing the nuclei to generate permeabilized nuclei.

16. The method of claim 15, comprising fixing the plurality of cells prior to permeabilizing the nuclei.

17. The method of claim 1, wherein the dsDNA is selected from the group consisting of: nuclear DNA, nucleolar DNA, genomic DNA, or any combination thereof.

18. The method of claim 2, wherein determining the chromatin accessibility of the dsDNA comprises:
aligning the sequences of the plurality of barcoded amplicons to a reference sequence of the dsDNA; and
identifying regions of the dsDNA corresponding to the ends of barcoded amplicons of the plurality of barcoded amplicons to have an accessibility above a threshold.

19. The method of claim 2, wherein determining the chromatin accessibility of the dsDNA comprises:
aligning the sequences of the plurality of barcoded amplicons to a reference sequence of the dsDNA; and
determining the accessibility of regions of the dsDNA corresponding the ends of barcoded amplicons of the plurality of barcoded amplicons based on the numbers of the barcoded amplicons of the plurality of barcoded amplicons in the sequencing data.

20. The method of claim 2, comprising, for each unique cell label sequence, which indicates a single cell of the plurality of cells, determining the sequences of the plurality of barcoded amplicons associated with each cell label sequence in the sequencing data, thereby determining the chromatin accessibility of the dsDNA of each cell of the plurality of cells.

21. The method of claim 1, wherein at least one barcode of the plurality of barcodes is:
immobilized on the bead;
partially immobilized on the bead;
enclosed in the bead; and/or
partially enclosed in the bead.

22. The method of claim 1, wherein the bead is disruptable upon application of a chemical stimulus, and wherein the method comprises contacting the partitions with the chemical stimulus, thereby releasing the associated barcodes.

23. The method of claim 22, wherein the chemical stimulus is a reducing agent.

24. The method of claim 1, wherein the bead comprises a disruptable hydrogel bead.

25. The method of claim 1,
wherein the bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo (dT) conjugated bead, a silica bead, a silica-like bead, an anti-biotin microbead, an anti-fluorochrome microbead, or any combination thereof; and/or
wherein the bead comprises a material selected from the group comprising polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof.

26. The method of claim 1, wherein a dsDNA fragment of the plurality of dsDNA fragments is flanked by a first adaptor and a second adaptor.

27. The method of claim 1, wherein the plurality of cells is a plurality of single cells and/or the sample is a tissue.

28. The method of claim 1, wherein the moiety comprises an antibody or fragment thereof, an apatmer, or a DNA binding domain.

29. The method of claim 28, wherein the antibody or fragment thereof specifically binds a histone protein.

30. The method of claim 28, wherein the DNA binding domain comprises a zinc finger binding domain.

* * * * *